United States Patent
Whiteker et al.

(10) Patent No.: US 8,609,855 B2
(45) Date of Patent: Dec. 17, 2013

(54) PROCESS FOR THE PREPARATION OF 4-AMINO-5-FLUORO-3-HALO-6-(SUBSTITUTED)PICOLINATES

(75) Inventors: Gregory T. Whiteker, Carmel, IN (US); Kim E. Arndt, Carmel, IN (US); Cynthia Arndt, legal representative, Carmel, IN (US); James M. Renga, Indianapolis, IN (US); Yuanming Zhu, Carmel, IN (US); Christian T. Lowe, Westfield, IN (US); Thomas L. Siddall, Zionsville, IN (US); David E. Podhorez, Midland, MI (US); Gary A. Roth, Midland, MI (US); Scott P. West, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/356,691

(22) Filed: Jan. 24, 2012

(65) Prior Publication Data

US 2012/0190860 A1  Jul. 26, 2012

Related U.S. Application Data

(60) Provisional application No. 61/435,958, filed on Jan. 25, 2011.

(51) Int. Cl.
*C07D 213/73* (2006.01)

(52) U.S. Cl.
USPC .......................................................... 546/310

(58) Field of Classification Search
None
See application file for complete search history.

(56) References Cited

U.S. PATENT DOCUMENTS

| | | |
|---|---|---|
| 3,285,925 A | 11/1966 | Johnston et al. |
| 3,325,272 A | 6/1967 | Hamaker |
| 3,629,424 A | 12/1971 | Torba |
| 3,803,159 A | 4/1974 | Torba |
| 6,297,197 B1 | 10/2001 | Fields et al. |
| 6,784,137 B2 | 8/2004 | Balko et al. |
| 7,314,849 B2 | 1/2008 | Balko |
| 7,432,227 B2 | 10/2008 | Balko |
| 2009/0088322 A1 | 4/2009 | Epp et al. |
| 2010/0041556 A1 | 2/2010 | Epp et al. |

*Primary Examiner* — Zinna Northington Davis
(74) *Attorney, Agent, or Firm* — Robert Chang; Craig E. Mixan

(57) ABSTRACT

4-Amino-5-fluoro-3-halo-6-(substituted)picolinates are conveniently prepared from 4,5,6-trichloropicolinates by a series of steps involving fluorine exchange, amination, halogen exchange, halogenation and transition metal assisted coupling.

4 Claims, No Drawings

PROCESS FOR THE PREPARATION OF 4-AMINO-5-FLUORO-3-HALO-6-(SUBSTITUTED)PICOLINATES

CROSS REFERENCE TO RELATED APPLICATIONS

This application claims the benefit of U.S. Provisional Patent Application Ser. No. 61/435,958 filed Jan. 25, 2011.

FIELD OF THE INVENTION

The present invention concerns a process for the preparation of 4-amino-5-fluoro-3-halo-6-(substituted)picolinates. More particularly, the present invention concerns a process for the preparation of 4-amino-5-fluoro-3-halo-6-(substituted)picolinates in which the 5-fluoro substituent is introduced by a halogen exchange early in the process scheme.

BACKGROUND OF THE INVENTION

U.S. Pat. No. 6,297,197 B1 describes inter alia certain 6-(alkoxy or aryloxy)-4-amino-3-chloro-5-fluoropicolinate compounds and their use as herbicides. U.S. Pat. Nos. 6,784,137 B2 and 7,314,849 B2 describe inter alia certain 6-(aryl)-4-amino-3-chloro-5-fluoropicolinate compounds and their use as herbicides. U.S. Pat. No. 7,432,227 B2 describes inter alia certain 6-(alkyl)-4-amino-3-chloro-5-fluoropicolinate compounds and their use as herbicides. Each of these patents describes the manufacture of 4-amino-3-chloro-5-fluoropicolinate starting materials by fluorination of the corresponding 5-unsubstituted pyridines with 1-(chloromethyl)-4-fluoro-1,4-diazoniabicyclo[2.2.2]octane bis(tetrafluoroborate). It would be advantageous to produce 4-amino-5-fluoro-3-halo-6-(substituted)picolinates without having to rely on direct fluorination of the 5-position of the pyridine ring with an expensive fluorinating agent like 1-(chloromethyl)-4-fluoro-1,4-diazoniabicyclo[2.2.2]octane bis(tetrafluoroborate).

SUMMARY OF THE INVENTION

The present invention concerns a process for the preparation of 4-amino-5-fluoro-3-halo-6-(substituted)picolinates from 4,5,6-trichloropicolinates. More particularly, the present invention concerns a process for the preparation of a 4-amino-5-fluoro-3-halo-6-(substituted)picolinate of the Formula I

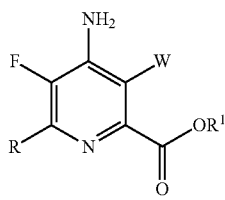

I wherein
W represents Cl, Br or I;
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl;
which comprises the following steps:
a) fluorinating a 4,5,6-trichloropicolinate of Formula A

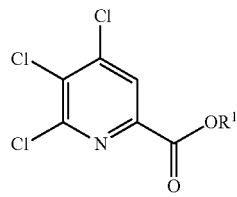

A wherein $R^1$ is as previously defined;
with a source of fluoride ion to produce a 4,5,6-trifluoropicolinate of Formula B

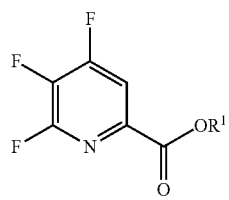

B wherein $R^1$ is as previously defined;
b) aminating the 4,5,6-trifluoropicolinate of Formula B with ammonia to produce a 4-amino-5,6-difluoropicolinate of Formula C

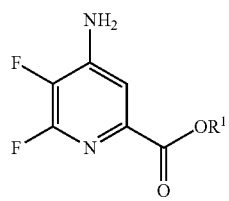

C wherein $R^1$ is as previously defined;
c) exchanging the fluoro substituent in the 6-position of the 4-amino-5,6-difluoropicolinate of Formula C with an iodo, bromo or chloro substituent by treating with an iodide, bromide or chloride source to produce a 4-amino-5-fluoro-6-halopicolinate of Formula D

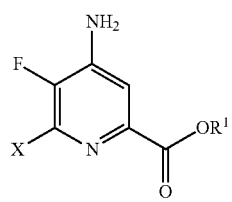

D wherein X represents Cl, Br or I;
and $R^1$ is as previously defined;
d) halogenating the 4-amino-5-fluoro-6-halopicolinate of Formula D with a halogen source to produce a 4-amino-3,6-dihalo-5-fluoropicolinate of Formula E

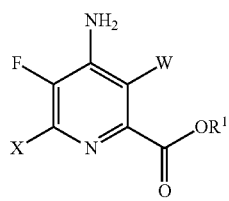

wherein W and X independently represent Cl, Br or I; and R¹ is as previously defined; and e) coupling the 4-amino-3,6-dihalo-5-fluoropicolinate of Formula E with an aryl, alkyl or alkenyl metal compound of the Formula F R-Met      F wherein R is as previously defined and Met represents Zn-halide, Zn—R, tri-($C_1$-$C_4$ alkyl)tin, copper, or B(OR²)(OR³), where R² and R³ are independent of one another, hydrogen, $C_1$-$C_4$ alkyl, or when taken together form an ethylene or propylene group in the presence of a transition metal catalyst to produce the 4-amino-5-fluoro-3-halo-6-(substituted)picolinate of Formula I.

The steps a) through e) may be performed in the order listed, as depicted in Scheme I.

Scheme I

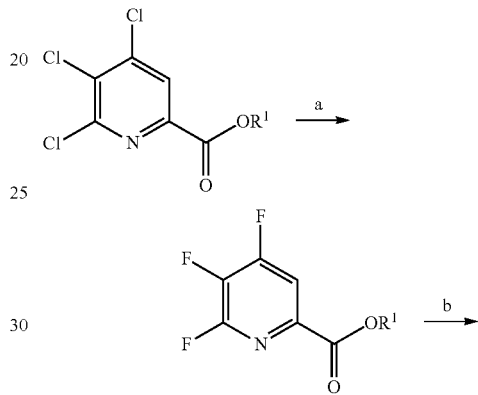

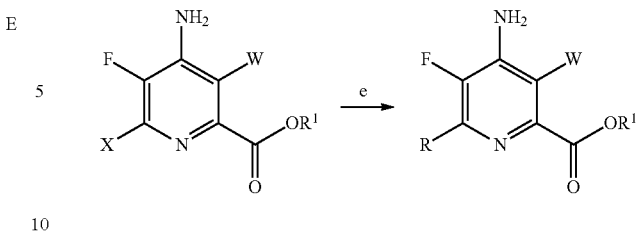

Alternatively, the order in which the steps are performed can be rearranged as illustrated, for example, in Schemes II and III.

Scheme II

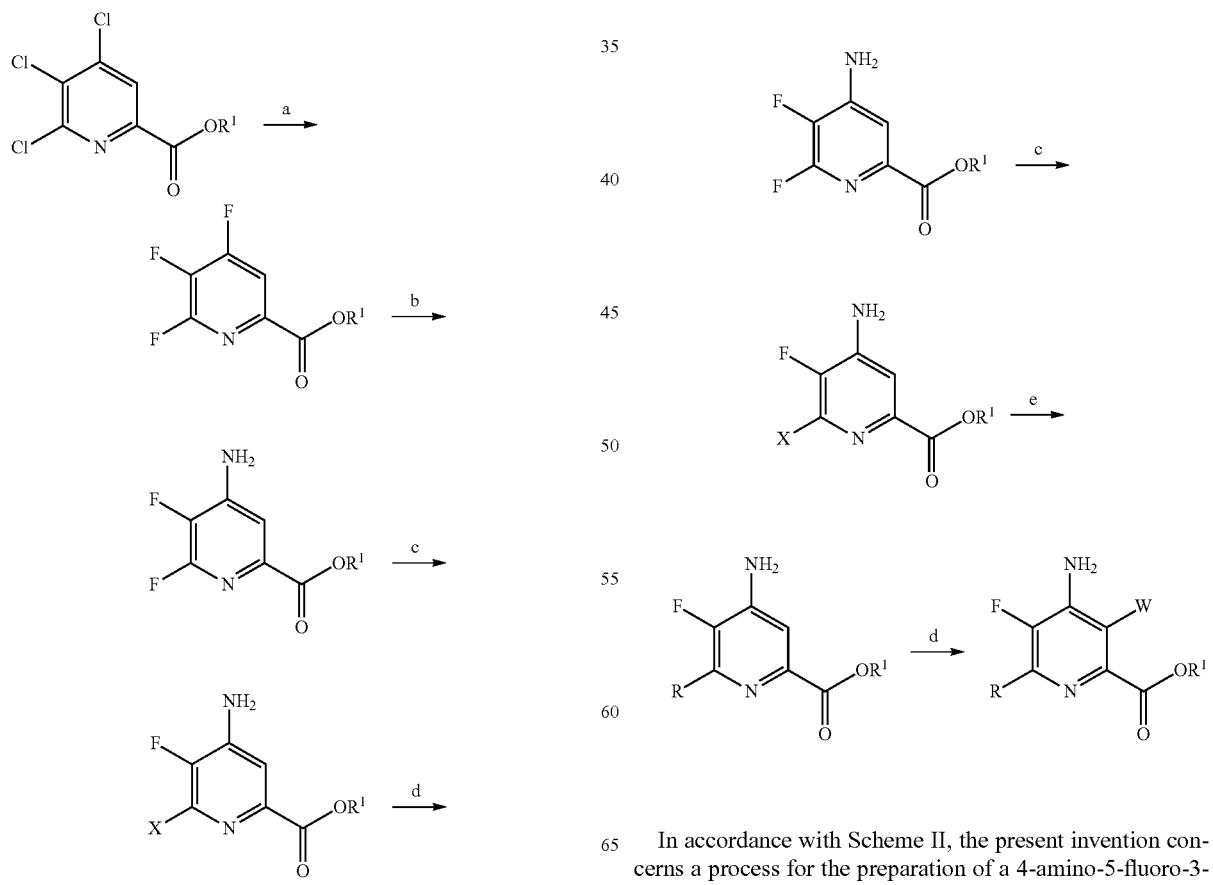

In accordance with Scheme II, the present invention concerns a process for the preparation of a 4-amino-5-fluoro-3-halo-6-(substituted)picolinate of the Formula I

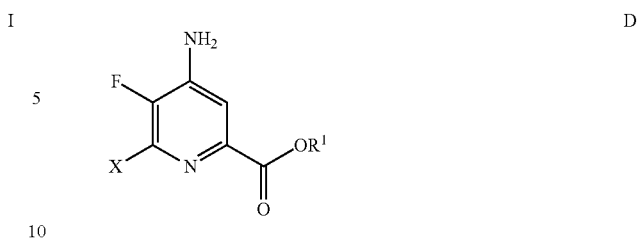

wherein
W represents Cl, Br or I;
R represents C$_1$-C$_4$ alkyl, cyclopropyl, C$_2$-C$_4$ alkenyl, or phenyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy; and
R$^1$ represents C$_1$-C$_{12}$ alkyl or an unsubstituted or substituted C$_7$-C$_{11}$ arylalkyl; which comprises the following steps:
a) fluorinating a 4,5,6-trichloropicolinate of Formula A

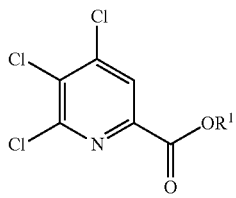

wherein R$^1$ is as previously defined;
with a source of fluoride ion to produce a 4,5,6-trifluoropicolinate of Formula B

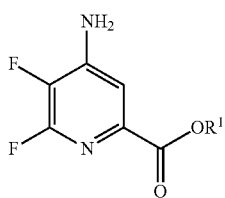

wherein R$^1$ is as previously defined;
b) aminating the 4,5,6-trifluoropicolinate of Formula B with ammonia to produce a 4-amino-5,6-difluoropicolinate of Formula C

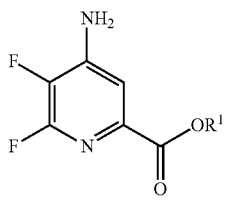

wherein R$^1$ is as previously defined;
c) exchanging the fluoro substituent in the 6-position of the 4-amino-5,6-difluoro picolinate of Formula C with an iodo, bromo or chloro substituent by treating with an iodide, bromide or chloride source to produce a 4-amino-5-fluoro-6-halopicolinate of Formula D

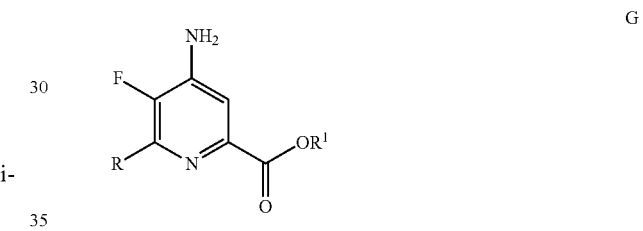

wherein X represents Cl, Br or I; and
R$^1$ is as previously defined;
d) coupling the 4-amino-5-fluoro-6-halopicolinate of Formula D with an aryl, alkyl or alkenyl metal compound of the Formula F R-Met  F wherein R is as previously defined and Met represents Zn-halide, Zn—R, tri-(C$_1$-C$_4$ alkyl)tin, copper, or B(OR$^2$)(OR$^3$), where R$^2$ and R$^3$ are independent of one another, hydrogen, C$_1$-C$_4$ alkyl, or when taken together form an ethylene or propylene group in the presence of a transition metal catalyst to produce the 4-amino-5-fluoro-6-(substituted)-picolinate of Formula G.

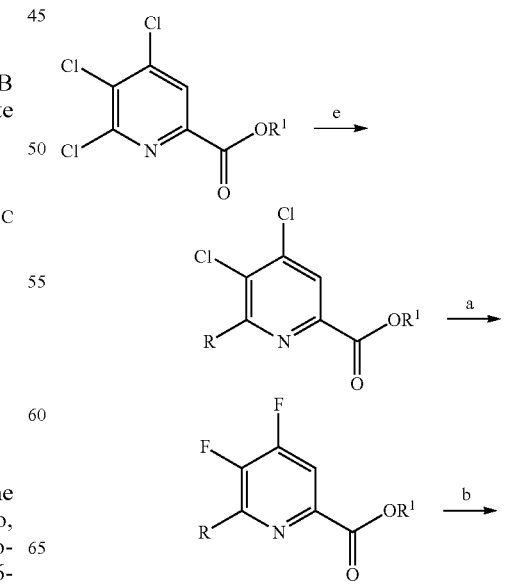

wherein R and R$^1$ are as previously defined; and
e) halogenating the 4-amino-5-fluoro-6-(substituted)picolinate of Formula G with a halogen source to produce a 4-amino-5-fluoro-3-halo-6-(substituted)picolinate of Formula I.

Scheme III

-continued

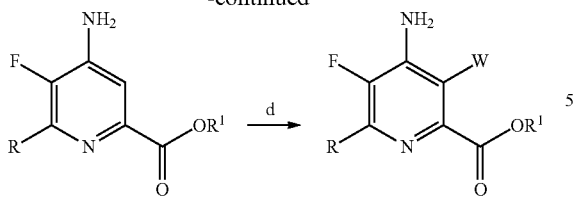

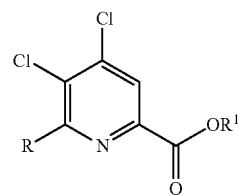

In Scheme III, the iodine, bromine or chlorine exchange step c) is not necessary. Thus, the present invention also concerns a process for the preparation of a 4-amino-5-fluoro-3-halo-6-(substituted)picolinate of the Formula I

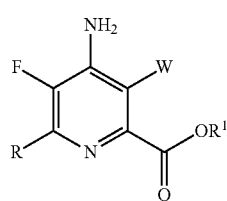

wherein

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; which comprises the following steps:

a) coupling a 4,5,6-trichloropicolinate of Formula A

A

[structure shown]

wherein $R^1$ is as previously defined;

with an aryl, alkyl or alkenyl metal compound of the Formula F

R-Met    F wherein R is as previously defined and Met represents Zn-halide, Zn—R, tri-($C_1$-$C_4$ alkyl)tin, copper, or B(OR$^2$)(OR$^3$), where $R^2$ and $R^3$ are independent of one another, hydrogen, $C_1$-$C_4$ alkyl, or when taken together form an ethylene or propylene group in the presence of a transition metal catalyst to produce a 4,5-dichloro-6-(substituted)picolinate of Formula H

H

[structure shown]

wherein R and $R^1$ are as previously defined;

b) fluorinating the 4,5-dichloro-6-(substituted)picolinate of Formula H with a fluoride ion source to produce a 4,5-difluoro-6-(substituted)picolinate of Formula J

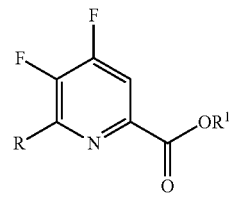

wherein $R^1$ is as previously defined;

c) aminating the 4,5-difluoro-6-(substituted)picolinate of Formula J with ammonia to produce a 4-amino-5-fluoro-6-(substituted)picolinate of Formula K

K

[structure shown]

wherein R and $R^1$ are as previously defined; and d) halogenating the 4-amino-5-fluoro-6-(substituted)picolinate of Formula K with a halogen source to produce the 4-amino-5-fluoro-3-halo-6-(substituted)picolinate of Formula I.

At any step in Schemes I-III, the ester substituent, $R^1$, may optionally be exchanged with a different $R^1$ substituent. These esters, including unsubstituted or substituted $C_7$-$C_{11}$ arylalkyl esters, can be prepared by direct esterification or transesterification reactions using techniques which are well known in the art.

Another aspect of the present invention is the novel intermediates produced during the present process, viz., compounds selected from the group consisting of:

a)

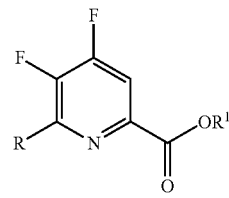

wherein R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy and $R^1$ represents $C_1$-$C_{12}$ alkyl or an unsubstituted or substituted $C_7$-$C_{11}$ arylalkyl;

b)

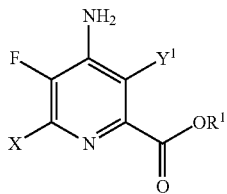

wherein X represents I, Br, Cl or F, $Y^1$ represents H, Cl, Br, or I with the proviso that when X is Cl, $Y^1$ is H, Br or I, and $R^1$ represents $C_1$-$C_{12}$ alkyl or an unsubstituted or substituted $C_7$-$C_{11}$ arylalkyl;

c)

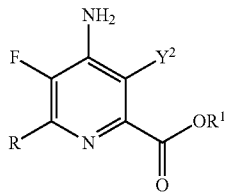

wherein $Y^2$ represents H, Br or I, and R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and $R^1$ represents $C_1$-$C_{12}$ alkyl or an unsubstituted or substituted $C_7$-$C_{11}$ arylalkyl; and d)

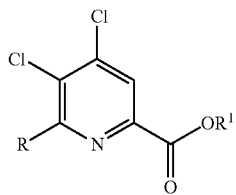

wherein R represents $C_1$-$C_4$ alkyl, cyclopropyl, $C_2$-$C_4$ alkenyl, or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and $R^1$ represents $C_1$-$C_{12}$ alkyl or an unsubstituted or substituted $C_7$-$C_{11}$ arylalkyl.

DETAILED DESCRIPTION OF THE INVENTION

The terms "alkyl," "alkenyl" and "alkynyl," as well as derivative terms such as "alkoxy," "acyl," "alkylthio" and "alkylsulfonyl," as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "arylalkyl," as used herein, refers to a phenyl substituted alkyl group having a total of 7 to 11 carbon atoms, such as benzyl (—$CH_2C_6H_5$), 2-methylnaphthyl (—$CH_2C_{10}H_7$) and 1- or 2-phenethyl (—$CH_2CH_2C_6H_5$ or —$CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, $C(O)OC_1$-$C_6$alkyl, or where two adjacent substituents are taken together as —$O(CH_2)_nO$— wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

The 6-phenyl groups substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

The 4-amino-5-fluoro-3-halo-6-(substituted)picolinates are prepared from 4,5,6-trichloropicolinates by a series of steps involving fluorine exchange, amination, halogen exchange, halogenation and transition metal assisted coupling. The individual steps may be performed in different sequences.

The 4,5,6-trichloropicolinate starting materials are known compounds; see, for example, Example 3 in U.S. Pat. No. 6,784,137 B2. Higher esters, including unsubstituted or substituted $C_7$-$C_{11}$ arylalkyl esters, can be prepared by direct esterification or transesterification reactions using techniques which are well known in the art.

In the fluorine exchange reaction, the fluorinated picolinate is prepared by reacting the corresponding chlorinated picolinate with at least one equivalent of fluoride ion source for each ring chlorine substituent to be exchanged.

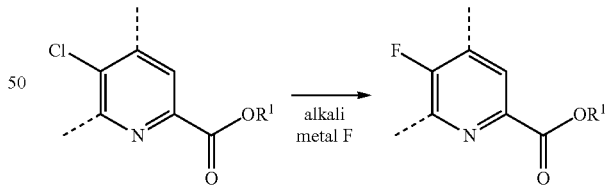

Typical fluoride ion sources are alkali metal fluorides which include sodium fluoride (NaF), potassium fluoride (KF) and cesium fluoride (CsF), with KF and CsF being preferred. Fluoride salts such as tetrabutylammonium fluoride (n-$Bu_4$NF) may also be used. Preferably, the reaction is carried out in a polar aprotic solvent or reaction medium such as, dimethylsulfoxide (DMSO), N-methylpyrrolidinone (NMP), N,N-dimethylformamide (DMF), hexamethylphosphoramide (HMPA) or sulfolane. Additives such as crown ethers or phase transfer agents which are known to increase the rate of fluoride exchange may also be used. The temperature at which the reaction is conducted is not critical but usually is from about 70° C. to about 180° C. and preferably from about 80° C. to about 120° C. Depending upon which solvent is employed in a particular reaction, the optimum temperature will vary. Generally speaking the lower the temperature the slower the reaction will proceed. The present reaction is typically conducted in the presence of vigorous agitation sufficient to maintain an essentially uniformly dispersed mixture of the reactants.

In conducting the fluorination reaction, neither the rate, nor the order, of addition of the reactants is critical. Usually, the solvent and alkali metal fluoride are mixed before the chlorinated picolinate is added to the reaction mixture. A typical reaction generally requires from about 2 to about 100 hours and is usually conducted at ambient atmospheric pressure.

While the exact amount of reactants is not critical, it is preferred to employ an amount of alkali metal fluoride which will supply at least about an equimolar amount of fluorine atoms based on the number of chlorine atoms to be exchanged in the starting material, i.e., at least an equimolar amount of alkali metal fluoride. After the reaction is completed the desired product is recovered by employing standard separation and purification techniques.

In the amination, a 4-fluoropicolinate is allowed to react with ammonia to replace the fluorine atom with an amino group.

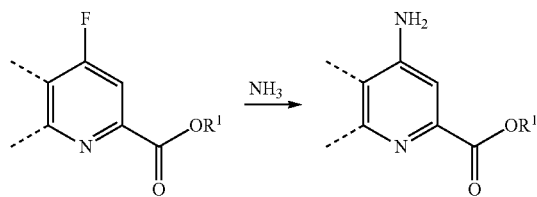

While only a stoichiometric amount of ammonia is required, it is often convenient to use a large excess of ammonia. The reaction is carried out in an inert solvent, preferably, a polar aprotic solvent or reaction medium such as DMSO, NMP, DMF, HMPA or sulfolane. Alternatively, aqueous ammonium hydroxide can be used, with or without use of an organic solvent. The temperature at which the reaction is conducted is not critical but usually is from about 0° C. to about 45° C. and preferably from about 10° C. to about 30° C.

In conducting the amination reaction, the 4-fluoropicolinate is dissolved in the solvent, and the ammonia is added to the reaction mixture with cooling. Excess ammonia gas is typically bubbled into the reaction mixture. A typical reaction generally requires from about 0.5 to about 5 hours and is usually conducted at ambient atmospheric pressure.

The amine-containing products or intermediates obtained by any of these processes can be recovered by conventional means, such as evaporation or extraction, and can be purified by standard procedures, such as recrystallization or chromatography. Purification of the amine-containing products or intermediates can also be affected by protonation with an acid to form a salt which is isolated in higher purity by crystallization, precipitation or extraction. A variety of acids, such as hydrochloric acid, hydrobromic acid, nitric acid, acetic acid or sulfuric acid, can be used. Anhydrous hydrochloric acid is a preferred acid. The purified salt is then neutralized with a base to form the neutral amine-containing product or intermediate. Inorganic bases, such as sodium hydroxide, potassium hydroxide, potassium carbonate, sodium carbonate or sodium bicarbonate may be used. Organic bases such as triethylamine are preferred. Purification of the amine-containing product or intermediate may be performed in this manner immediately after the amination step, or after subsequent reactions, e.g., halogenation, coupling, have been preformed.

In the halogen (iodine, bromine or chlorine) exchange reaction, the 6-iodinated, 6-brominated or 6-chlorinated picolinate is prepared by reacting the corresponding 6-fluorinated picolinate with at least one equivalent of iodide, bromide or chloride.

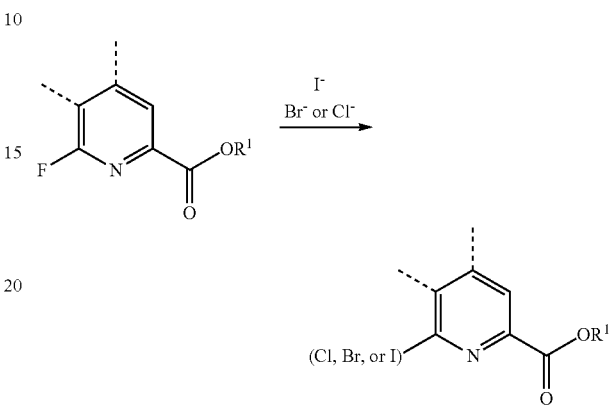

Typically, the halogen exchange reaction is carried out in the presence of a large excess of anhydrous hydrogen iodide (HI), hydrogen bromide (HBr) or hydrogen chloride (HCl). The reaction is typically performed in the absence of water to minimize the formation of by-products. The halogen exchange generally requires from about 5 to about 50 equivalents of HI, HBr or HCl, preferably from 10 to 20 equivalents. The reaction is carried out in an inert solvent, preferably, a polar solvent such as dioxane or acetic acid. The temperature at which the reaction is conducted is not critical but usually is from about 75° C. to about 150° C. and preferably from about 100° C. to about 125° C. The reaction is typically performed in a sealed pressure reactor which is capable of containing HI, HBr or HCl gas. A typical reaction generally requires from about 0.5 to about 5 hours.

In the halogenation reaction, a chlorine, bromine or iodine atom is introduced into the 3-position of the picolinate by reacting the 3-unsubstituted picolinate with a halogen source in an inert solvent.

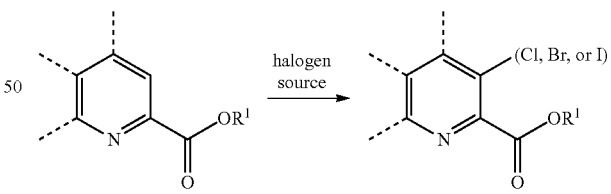

When the halogen atom at the 3-position is Cl, the chlorine source can be chlorine ($Cl_2$) itself or reagents such as sulfuryl chloride, N-chlorosuccinimide or 1,3-dichloro-5,5-dimethylhydantoin. When chlorine or sulfuryl chloride are used, a large excess of chlorinating agent is used. When chlorine gas is used, the reaction is performed in an inert solvent, preferably, a solvent such as dichloromethane, dichloromethane-water or acetic acid. When sulfuryl chloride is used, the reaction can be performed in an inert solvent, such as dichloromethane or in neat sulfuryl chloride. The temperature at which the reaction is conducted is not critical but usually is from about 0° C. to about 45° C. and preferably from about 10° C. to about 30° C. A typical reaction generally requires from about 0.5 to about 5 hours. The chlorination reaction is usually conducted at ambient atmospheric pressure.

When the chlorinating agent used is N-chlorosuccinimide or 1,3-dichloro-5,5-dimethylhydantoin, the reaction is carried out using a stoichiometric amount of chlorinating reagent. For chlorinations using 1,3-dichloro-5,5-dimethylhydantoin as the chlorinating agent, both chlorines in the hydantoin are found to react. The reaction is performed in an inert polar solvent, such as DMF or acetonitrile. The temperature at which the reaction is conducted is not critical but usually is from about 20° C. to about 85° C. and preferably from about 50° C. to about 80° C. When acetonitrile is used as solvent, it is convenient to carry out the reaction at the reflux temperature. A typical reaction generally requires from about 0.5 to about 5 hours. The chlorination reaction is usually conducted at ambient atmospheric pressure.

When the halogen atom at the 3-position is Br, the bromine source can be bromine ($Br_2$) itself or reagents such as sulfuryl bromide, N-bromosuccinimide or 1,3-dibromo-5,5-dimethylhydantoin. When $Br_2$ is used as the brominating agent, a large excess can be employed, and the reaction is performed in an inert solvent, preferably, a solvent such as dichloromethane, dichloromethane-water or acetic acid. The temperature at which the reaction is conducted is not critical but usually is from about 0° C. to about 45° C. and preferably from about 10° C. to about 30° C. A typical reaction generally requires from about 0.5 to about 5 hours. The bromination reaction is usually conducted at ambient atmospheric pressure.

When the brominating agent used is N-bromosuccinimide or 1,3-dibromo-5,5-dimethylhydantoin, the reaction is carried out using a stoichiometric amount of brominating reagent. The reaction is performed in an inert polar solvent, such as DMF or acetonitrile. The temperature at which the reaction is conducted is not critical but usually is from about 20° C. to about 85° C. and preferably from about 50° C. to about 80° C. When acetonitrile is used as solvent, it is convenient to carry out the reaction at the reflux temperature. A typical reaction generally requires from about 0.5 to about 5 hours. The bromination reaction is usually conducted at ambient atmospheric pressure.

When the halogen atom at the 3-position is I, the iodine source can be iodine ($I_2$) itself or reagents such as iodine monochloride or N-iodosuccinimide Periodic acid may be used in conjunction with $I_2$. When $I_2$ is used as the iodinating agent, a large excess of $I_2$ can be employed, and the reaction is performed in an inert solvent, preferably, a solvent such as dichloromethane, dichloromethane-water, methyl alcohol or acetic acid. The temperature at which the reaction is conducted is not critical but usually is from about 0° C. to about 45° C. and preferably from about 10° C. to about 30° C. A typical reaction generally requires from about 0.5 to about 5 hours. The iodination reaction is usually conducted at ambient atmospheric pressure.

In the coupling reaction, a 6-iodo, bromo or chloropicolinate is reacted with an aryl, alkyl or alkenyl metal compound where the metal is a Zn-halide, Zn—R, tri-($C_1$-$C_4$ alkyl)tin, copper, or $B(OR^2)(OR^3)$, where $R^2$ and $R^3$ are independent of one another, hydrogen, $C_1$-$C_4$ alkyl, or when taken together form an ethylene or propylene group, in the presence of a transition metal catalyst.

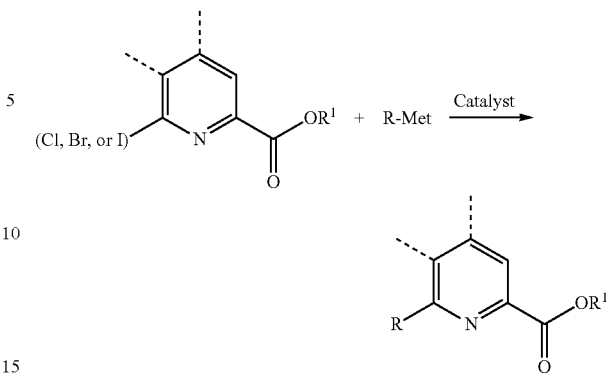

"Catalyst" is a transition metal catalyst, in particular a palladium catalyst such as palladium diacetate or bis(triphenylphosphine)palladium(II) dichloride, or a nickel catalyst such as nickel(II) acetylacetonate or bis(triphenylphosphine) nickel(II) dichloride. In addition, catalysts can be prepared in situ from metal salts and ligands, such as palladium acetate and triphenylphosphine or nickel(II) chloride and triphenylphosphine. These in situ catalysts can be prepared by prior reaction of metal salt and ligand, followed by addition to the reaction mixture, or by separate addition of the metal salt and ligand directly to the reaction mixture.

Typically, coupling reactions are carried out in the absence of oxygen using an inert gas, such as nitrogen or argon. Techniques used to exclude oxygen from coupling reaction mixtures, such as sparging with inert gas, are well known to those skilled in the art. Examples of such techniques are described in *The Manipulation of Air-Sensitive Compounds*, $2^{nd}$ ed.; Shriver, D. F., Drezdzon, M. A., Eds.; Wiley-Interscience, 1986. Sub-stoichiometric amounts of a catalyst are used, typically from about 0.0001 equivalents to 0.1 equivalents. Additional amounts of ligand may optionally be added to increase catalyst stability and activity. In addition, additives such as $Na_2CO_3$, $K_2CO_3$, KF, CsF and NaF are typically added to the coupling reaction. The coupling reaction generally requires from about 1 to about 5 equivalents of such additive, preferably from 1 to 2 equivalents. Water may optionally be added to the coupling reaction to increase the solubility of these additives. The coupling reaction generally requires from 1 to about 3 equivalents of an aryl, alkyl or alkenyl metal compound, preferably from 1 to 1.5 equivalents. The reaction is carried out in an inert solvent, such as toluene, tetrahydrofuran (THF), dioxane or acetonitrile. The temperature at which the reaction is conducted is not critical but usually is from about 25° C. to about 150° C. and preferably from about 50° C. to about 125° C. A typical reaction generally requires from about 0.5 to about 24 hours. No particular order of addition of reactants is typically required. It is often operationally simpler to combine all reactants except the catalyst and then deoxygenate the reaction solution. Following deoxygenation, the catalyst can be added to commence the coupling reaction.

When the Met portion of the aryl, alkyl or alkenyl metal compound is a Zn-halide, Zn—R or copper, protection of reactive functional groups may be necessary. For example, if an amino substituent (—NHR or —$NH_2$) is present, protection of these reactive groups may be required. A variety of groups are known in the art for protection of amino groups from reaction with organometallic reagents. Examples of such protecting groups are described in *Protective Groups in Organic Synthesis*, $3^{rd}$ ed.; Greene, T. W.; Wuts, P. G. M., Eds.; Wiley-Interscience, 1999. The choice of which metal to use in R-Met is influenced by a number of factors, such as cost, stability, reactivity and the need to protect reactive functional groups.

The products obtained by any of these processes can be recovered by conventional means, such as evaporation or extraction, and can be purified by standard procedures, such as recrystallization or chromatography.

The following examples are presented to illustrate the invention.

EXAMPLES

Preparation of Starting Material

Example A

Propan-2-yl 4,5,6-trichloropicolinate

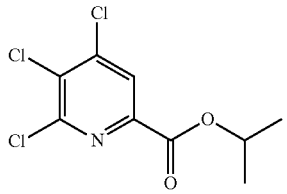

Methyl 4,5,6-trichloropicolinate (14.19 grams (g), 59.0 millimoles (mmol)) was slurried in 2-propanol (150 milliliters (mL)) in a 250 mL round bottom flask equipped with a Dean-Stark trap and a reflux condenser. Sulfuric acid (98% $H_2SO_4$; 8.07 g, 82 mmol) was added, and the reaction mixture was heated to reflux. After 20 hours (h) at reflux, the majority of the 2-propanol (100 mL) was distilled overhead. The pot solidified upon cooling to room temperature. The resulting solid was stirred with ethyl acetate (EtOAc; 500 mL) and saturated (satd) aqueous (aq) sodium bicarbonate solution ($NaHCO_3$; 500 mL). The organic layer was separated, washed with brine and then filtered through Celite. The organic extract was concentrated to 150 mL by rotary evaporation. Hexane (100 mL) was added, and the solution was stored at −20° C. overnight. Crystals were collected, washed with hexane and dried in air (7.58 g, mp 104.6-105.7° C.). A second crop was obtained by concentration of the filtrate to give a total of 10.36 g (65%) $^1H$ NMR (400 MHz, DMSO-$d_6$) δ 8.23 (s, 1H, pyridine H), 5.16 (septet, J=6.3 Hz, 1H, CHMe$_2$), 1.34 (d, J=6.3 Hz, 6H, CHMe$_2$); $^{13}C\{^1H\}$ NMR (101 MHz, CDCl$_3$) δ 161.9 (CO$_2$R), 150.6, 145.9, 145.0, 133.1, 125.4 (C3), 70.7 (CHMe$_2$), 21.7 (Me). Anal. Calcd for $C_9H_8Cl_3NO_2$: C, 40.26; H, 3.00; N, 5.22. Found: C, 40.25; H, 3.02; N, 5.22.

Example B

Benzyl 4,5,6-trichloropicolinate

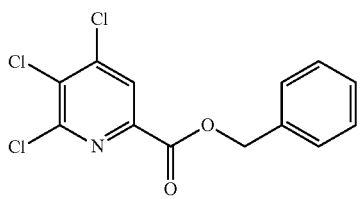 [SMILES: O=C(OCc1ccccc1)c1cc(Cl)c(Cl)c(Cl)n1]

A mixture of methyl 4,5,6-trichloropicolinate (25 g, 0.10 moles (mol)) and benzyl alcohol (100 g, 0.2 mol) in a 250 mL three-neck round bottom flask was heated under nitrogen at 100° C. Titanium isopropoxide (0.6 g, 0.02 mol) was added. After 4 h at 100° C., the nearly colorless solution was cooled and transferred to a 250 mL round bottom single neck flask. Excess benzyl alcohol was removed under vacuum to give a nearly white solid (31 g, 94%): mp 125-126.5° C.; $^1H$ NMR (400 MHz, CDCl$_3$) δ 8.08 (s, 1H, pyridine H), 7.42 (m, 2H, phenyl), 7.31 (m, 3H, phenyl), 5.40 (s, 2H, CH$_2$Ph); $^{13}C\{^1H\}$ NMR (101 MHz, CDCl$_3$) δ 162.0 (CO$_2$R), 150.4, 145.0, 144.9, 134.7, 133.1, 128.3 (phenyl CH), 125.4 (pyridine CH), 67.88 (CH$_2$Ph).

Example C

Benzyl 4,5,6-trichloropicolinate

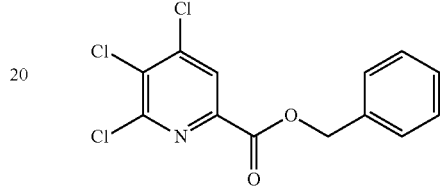

A 22 L round bottom flask was fitted with a thermocouple, mechanical stirrer and a Dean-Stark trap which was connected to a nitrogen bubbler. The vessel was purged with nitrogen and then 4,5,6-trichloropicolinate (2547 g, 10.07 mol), pyridinium p-toluene sulfonate (PPTS; 130 g, 0.52 mol), benzyl alcohol (2249 g, 20.8 mol) and xylenes (10278 g) were added. Stirring was started, and the pot was heated to 140 to 145° C. The xylenes/water azeotrope was collected in the Dean-Stark trap over about 5 h. The total amount of distillate collected was 4750 g (415 g was water). After the water stopped distilling overhead, a reactor sample was taken and analyzed by high-performance liquid chromatography (HPLC) to ensure less than 1.5 area % of starting carboxylic acid remained. The reaction was allowed to cool to room temperature and stirred overnight. Xylenes (4000 g) were removed by vacuum distillation. The solution was cooled to 85-100° C. and then vacuum transferred to a 30 L jacketed crystallization vessel that had been fitted with a mechanical stirrer and thermocouple. The vacuum was released with nitrogen and a nitrogen bubbler was placed on the crystallization vessel. To the xylene solution was added isopropyl alcohol (IPA; 6200 g) over about 15 minutes (min). The resulting slurry was allowed to cool slowly to room temperature and then cooled further to 5° C. The solid was collected by filtration, and the cake was washed with cold (5-10° C.) IPA (3731 g). The solid was dried in air to a constant weight providing white crystals (2765 g, gas chromatography (GC) internal standard purity 96.5%, 84.3%).

Fluorine Exchange

Example 1a

Propan-2-yl 4,5,6-trifluoropicolinate

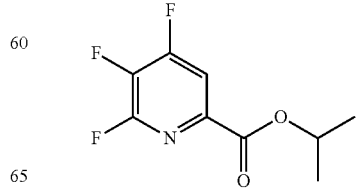

A 250 mL three-neck flask was equipped with a mechanical stirrer, a Dean-Stark trap with nitrogen inlet and a thermocouple. The flask was purged with nitrogen and CsF (23.38 g, 154 mmol) was added. Anhydrous DMSO (124 mL) was added, and the suspension was evacuated/backfilled (5×) with nitrogen. The suspension was heated at 80° C. for 30 min DMSO (20 mL) was distilled off under vacuum at 75° C. to remove any residual water. Propan-2-yl 4,5,6-trichloropicolinate (13.45 g, 50.1 mmol) was added against a nitrogen purge. The reaction mixture was evacuated/backfilled (3×) and heated at 100° C. for 1 h with vigorous stirring.

A second 250 mL three-neck flask was equipped with a mechanical stirrer, a Dean-Stark trap with nitrogen inlet and a thermocouple. The flask was purged with nitrogen and CsF (24.41 g, 0.160 mmol) was added. Anhydrous DMSO (30 mL) was added, and the suspension was evacuated/backfilled (5×) with nitrogen. The suspension was heated to 80° C. for 30 min. DMSO (22 mL) was distilled off under vacuum at 75° C. to remove residual water. The cooled reaction mixture in the first flask was cannula filtered into the second flask under nitrogen. The reaction mixture was evacuated/backfilled (5×) and then heated to 100° C. for 1 h and then for an additional 90 min at 110° C. Analysis of an aliquot by GC showed 96% propan-2-yl 4,5,6-trifluoropicolinate with only 1.4% propan-2-yl 5-chloro-4,6-difluoropicolinate present. The crude product solution was used directly in the amination step without further purification. Alternatively, the product can be isolated by aqueous workup, extraction with EtOAc and drying to give a light tan oil: $^1$H NMR (400 MHz, CDCl$_3$) δ 7.94 (dd, $J_{F-H}$=4.5, 8.7 Hz, 1H, H3), 5.30 (septet, $J_{H-H}$=6.3 Hz, 1H, CHMe$_2$), 1.44 (d, $J_{H-H}$=6.3 Hz, 6H, CHMe$_2$); $^{13}$C {$^1$H} NMR (101 MHz, CDCl$_3$) δ 161.2 (s, CO$_2$iPr), 157.3 (ddd, $J_{F-C}$=266, 8, 6 Hz, C4/C6), 152.2 (ddd, $J_{F-C}$=241, 12, 5 Hz, C4/C6), 141.1 (dt, $J_{F-C}$=14, 7 Hz, C2), 137.0 (ddd, $J_{F-C}$=270, 31, 13 Hz, C5), 113.8 (dd, $J_{F-C}$=17, 4 Hz, C3), 70.4 (s, CHMe$_2$), 21.33 (s, Me); $^{19}$F NMR (376 MHz, CDCl$_3$) δ −74.29 (dd, $J_{F-F}$=24, 22 Hz, F6), −112.67 (ddd, $J_{F-F}$=22, 19, $J_{F-H}$=8.3 Hz, F4), −151.58 (ddd, $J_{F-F}$=24, 19, $J_{F-H}$=4.7 Hz, F5).

Example 1b

Propan-2-yl 4,5-difluoro-6-(4-chloro-2-fluoro-3-methoxyphenyl)-picolinate

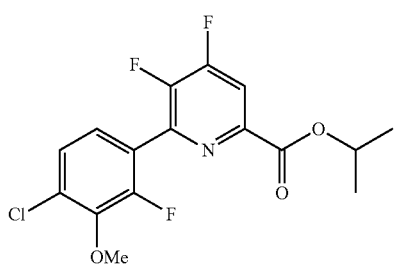 [SMILES: COc1c(Cl)ccc(-c2nc(C(=O)OC(C)C)cc(F)c2F)c1F]

A 250 mL three-neck flask was equipped with a distillation head, a nitrogen inlet, a mechanical stirrer and a thermocouple. The flask was charged with CsF (14.2 g, 93.0 mmol). Anhydrous DMSO (80 mL) was added, and the suspension was evacuated/backfilled (5×) with nitrogen. The suspension was heated at 80° C. for 30 min. DMSO (20 mL) was distilled off under vacuum to remove any residual water. Solid propan-2-yl 4,5-dichloro-6-(4-chloro-2-fluoro-3-methoxyphenyl)picolinate (10.44 g, 26.6 mmol) was added, and the solution was evacuated/backfilled with nitrogen (5×). The reaction mixture was heated to 105° C. under nitrogen. After 4 h at 105° C., analysis of an aliquot by GC showed a 91:6 ratio of difluoro to monofluoro products. The reaction mixture was allowed to cool to room temperature.

A second 250 mL three-neck flask was equipped with a mechanical stirrer, a distillation head with a nitrogen inlet and a thermocouple. The flask was purged with nitrogen and CsF (7.5 g, 49.4 mmol) was added. Anhydrous DMSO (20 mL) was added, and the suspension was evacuated/backfilled (5×) with nitrogen. The suspension was heated at 80° C. for 30 min DMSO (15 mL) was distilled off under vacuum to remove residual water. The cooled reaction mixture in the first flask was cannula filtered into the second flask under nitrogen. The reaction mixture was evacuated/backfilled (5×) and then heated to 100° C. for 2 h. Analysis of an aliquot by GC showed a 93:2 ratio of desired product to monofluoro intermediate. The reaction mixture was poured into ice-water (550 g) and was extracted with EtOAc (3×200 mL). The combined organic extracts were washed with water (5×100 mL) and brine, dried over magnesium sulfate (MgSO$_4$) and concentrated under reduced pressure to give a brown oil (8.57 g) which crystallized upon standing. The solid was purified by silica gel chromatography (330 g silica column; 0-50% EtOAc-hexane gradient) to give a white solid (4.98 g, 52%): mp 98.4-100.0° C.; $^1$H NMR (400 MHz, acetone-d$_6$) δ 8.16 (dd, $J_{F-H}$=10.0, 5.6 Hz, 1H, pyridine H), 7.43 (m, 2H, phenyl), 5.24 (hept, $J_{H-H}$=6.3 Hz, 1H, CHMe$_2$), 4.01 (d, $J_{F-H}$=1.1 Hz, 3H, OMe), 1.37 (d, $J_{H-H}$=6.3 Hz, 6H, CHMe$_2$); $^{13}$C{$^1$H} NMR (101 MHz, acetone-d$_6$) δ 163.1 (CO$_2$R), 157.1 (dd, $J_{F-C}$=264, 12 Hz, C4/C5), 154.8 (d, $J_{F-C}$=254 Hz, C2' phenyl), 148.6 (dd, $J_{F-C}$=267, 11 Hz, C4/C5), 147.4 (t, $J_{F-C}$=6 Hz), 145.5 (d, $J_{F-C}$=13 Hz), 144.6 (d, $J_{F-C}$=13 Hz), 131.0, 126.8, 126.6 (d, $J_{F-C}$=3.7 Hz), 123.2, 115.8 (d, $J_{F-C}$=16 Hz), 70.6 (CHMe$_2$), 62.1 (d, $J_{F-C}$=4 Hz, OMe), 21.9 (CHMe$_2$); $^{19}$F NMR (376 MHz, CDCl$_3$) δ −124.82 (dd, $J_{F-F}$=21 Hz, $J_{F-H}$=9.9 Hz, F4), −129.45 (dd, $J_{F-F}$=27.8 Hz, $J_{F-H}$=6.9 Hz, phenylF), −141.81 (m, F5). Anal. Calcd for C$_{16}$H$_{13}$ClF$_3$NO$_3$: C, 53.42; H, 3.64; N, 3.89. Found: C, 53.77; H, 3.70; N, 3.95. Analysis of an aliquot by GC showed that the product was 95.5% pure with 1.7% monofluoro impurity.

Example 1c

Benzyl 4,5-difluoro-6-(4-chloro-2-fluoro-3-methoxyphenyl)picolinate

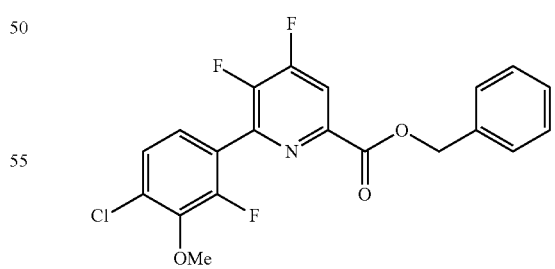

A 250 mL three-neck flask was equipped with a distillation head, a nitrogen inlet, a mechanical stirrer and a thermocouple. The flask was charged with CsF (21.07 g, 139.0 mmol). Anhydrous DMSO (100 mL) was added, and the suspension was evacuated/backfilled (5×) with nitrogen. The suspension was heated at 80° C. for 30 min DMSO (30 mL) was distilled off under vacuum to remove any residual water.

Solid benzyl 4,5-dichloro-6-(4-chloro-2-fluoro-3-methoxyphenyl)picolinate (15.34 g, 34.8 mmol) was added, and the solution was evacuated/backfilled with nitrogen (5×). The reaction mixture was heated to 105° C. under nitrogen. After 6 h at 105° C., analysis of an aliquot by GC showed no peak for the monofluoro intermediate. The reaction mixture was allowed to cool to room temperature. The reaction mixture was poured into ice-water (400 g) and was extracted with EtOAc (3×200 mL). The combined organic extracts were washed with satd NaHCO$_3$ solution, water (5×100 mL) and brine. The extracts were dried (MgSO$_4$) and concentrated under reduced pressure to give a tan solid (12.97 g). The solid was purified by flash chromatography (330 g silica column; 0-20% EtOAc-gradient) to give a white solid (9.95 g; 70%): mp 114-116° C.; $^1$H NMR (400 MHz, CDCl$_3$) δ 8.01 (dd, J$_{F-H}$=9.4, 5.5 Hz, 1H, pyridine H), 7.53-7.20 (m, 7H, phenyl), 5.44 (s, 2H, CH$_2$Ph), 3.99 (d, J$_{F-H}$=1.2 Hz, 3H, OMe); $^{13}$C NMR (101 MHz, CDCl$_3$) δ 162.8 (d, J$_{F-C}$=3 Hz, CO$_2$Bn), 156.2 (dd, J$_{F-C}$=267, 12 Hz), 153.9 (d, J$_{F-C}$=255 Hz), 148.0 (dd, J$_{F-C}$=269, 11 Hz), 145.4 (t, J$_{F-C}$=7 Hz), 144.7 (d, J$_{F-C}$=13 Hz), 144.6 (dd, J$_{F-C}$=13, 2 Hz), 135.2 (s), 130.6 (d, J$_{F-C}$=3 Hz), 125.6 (d, J$_{F-C}$=4 Hz), 125.4 (d, J$_{F-C}$=2 Hz), 122.0 (d, J$_{F-C}$=14 Hz), 115.0 (d, J$_{F-C}$=16 Hz), 67.9 (s, CH$_2$Ph), 61.6 (d, J$_{F-C}$=5 Hz, OMe); $^{19}$F{$^1$H} NMR (376 MHz, CDCl$_3$) δ −123.90 (d, J$_{F-F}$=19.7 Hz, F4), −128.37 (d, J$_{F-F}$=33.5 Hz, F2'), −139.64 (dd, J$_{F-F}$=33.5, 19.7 Hz, F5). Anal. Calcd for C$_{20}$H$_{13}$ClF$_3$NO$_3$: C, 58.91; H, 3.21; N, 3.43. Found: C, 59.03; H, 3.20; N, 3.39.

Example 1d

Benzyl 4,5-difluoro-6-(4-chloro-2-fluoro-3-methoxyphenyl)picolinate

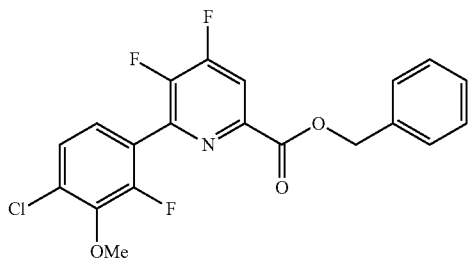 [SMILES: COc1c(Cl)ccc(-c2nc(C(=O)OCc3ccccc3)cc(F)c2F)c1F]

A 22 L straight wall jacketed reactor was fitted with an overhead stirrer, condenser, nitrogen inlet and outlet, and a stoppered solids loading port. The reactor was purged with nitrogen for 2 days. The loading port was opened, and benzyl 4,5-dichloro-6-(4-chloro-2-fluoro-3-methoxyphenyl)picolinate (2032 g, 4.12 mol, 89.3% purity) was quickly added to the reactor. CsF (2500 g, 16.46 mol) was quickly poured into the reactor. The reactor was next loaded with anhydrous (<100 ppm water) DMSO (8869 g). The mixture was heated to 110° C. for 2 h. The mixture was cooled to 35° C. and then filtered. The filtered salts were washed with DMSO (2×1108 g). The combined filtrate was cooled to 15-20° C., and water (3023 g) was added with stiffing over the course of 1 h. The mixture was cooled to 10-12° C. and then filtered. The collected solid was washed with 3:1 DMSO/water (1814 g) and then with water (2000 g). The resulting tan solid was dried to give the title compound (1626 g, 85.7 wt % HPLC purity (hexanophenone internal standard), 83%).

Amination

Example 2a

Propan-2-yl 4-amino-5,6-trifluoropicolinate

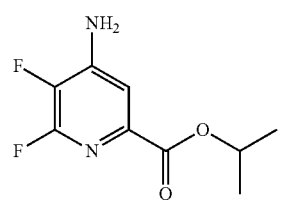

The reaction mixture from Example 1a was filtered to remove Cs salts, and the salts were washed with DMSO (50 mL). The DMSO washing solution was added to the DMSO solution (150 mL) which had been saturated with ammonia for 15 min. The flask was kept in a cold bath which kept the temperature near 16° C. Ammonia was bubbled through the reaction mixture for 30 min, during which time a white precipitate formed. After 90 min, analysis of an aliquot by GC showed a single major peak for the 4-amino product. The reaction mixture was quenched by addition of satd aq ammonium chloride (NH$_4$Cl) solution (100 mL) followed by water (400 mL). The aqueous solution was extracted into ether (Et$_2$O 3×150 mL) and then EtOAc (3×150 mL). The combined organic extracts were washed with water (5×150 mL) and then brine. The extracts were dried (MgSO$_4$) and evaporated to a tan solid which was washed with 1:1 hexane-ether to give a light tan powder (5.57 g, 51.4% overall): mp 168-170° C.; $^1$H NMR (400 MHz, CDCl$_3$) δ 7.42 (d, J$_{F-H}$=5.5 Hz, 1H, Pyridine H), 5.22 (septet, J=6.2 Hz, 1H, CHMe$_2$), 4.75 (s, 2H, NH$_2$), 1.35 (d, J=6.2 Hz, 6H, CHMe$_2$); $^{13}$C{$^1$H} NMR (101 MHz, DMSO-d$_6$) δ 162.8 (CO$_2$R), 151.2 (dd, J$_{F-C}$=228, 12 Hz, C6), 146.5 (dd, J$_{F-C}$=9, 6 Hz, C2/C4), 139.3 (dd, J$_{F-C}$=16, 5 Hz, C2/C4), 133.8 (dd, J$_{F-C}$=252, 31 Hz, C5), 112.3 (C3), 68.8 (CHMe$_2$), 21.5 (Me); $^{19}$F NMR (376 MHz, DMSO-d$_6$) δ −91.9 (d, J$_{F-F}$=26.6 Hz, F6), −163.9 (dd, J$_{F-F}$=26.6, J$_{H-F}$=5.6 Hz, F5). Anal. Calcd for C$_9$H$_{10}$F$_2$N$_2$O$_2$: C, 50.00; H, 4.66; N, 12.96. Found: C, 49.96; H, 4.65; N, 12.91.

Example 2b

Propan-2-yl 4-amino-5-fluoro-6-(4-chloro-2-fluoro-3-methoxyphenyl)-picolinate

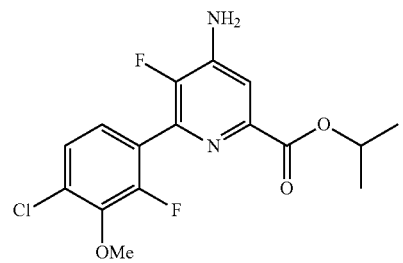 [SMILES: COc1c(Cl)ccc(-c2nc(C(=O)OC(C)C)cc(N)c2F)c1F]

Propan-2-yl 4,5-difluoro-6-(4-chloro-2-fluoro-3-methoxyphenyl)picolinate (4.89 g, 13.9 mmol) was dissolved in DMSO (100 mL). Ammonia was bubbled through the solution for a total of 100 min over the course of 48 h. The reaction mixture was poured into ice-water (500 mL). The product was extracted into EtOAc (3×250 mL). The combined organic extracts were washed with water (5×100 mL) and then brine, dried (MgSO$_4$) and concentrated under reduced pressure to give a white solid (4.36 g, 88%): mp 180.2-181.9° C.; $^1$H NMR (400 MHz, CDCl$_3$) δ 7.54 (d, $J_{F-H}$=6.5 Hz, 1H, pyridine H), 7.27 (m, 2H, phenyl), 5.27 (heptet, $J_{H-H}$=6.3 Hz, 1H, CHMe$_2$), 4.69 (s, 2H, NH$_2$), 3.96 (d, $J_{F-H}$=0.9 Hz, 3H, OMe), 1.38 (d, $J_{H-H}$=6.3 Hz, 6H, CHMe$_2$); $^{13}$C{$^1$H} NMR (101 MHz, DMSO-d$_6$) δ 163.7 (CO$_2$R), 153.2 (d, $J_{F-C}$=252 Hz), 146.8 (d, $J_{F-C}$=254 Hz), 144.2 (d, $J_{F-C}$=4 Hz), 143.9, 143.7, 139.0 (d, $J_{F-C}$=14 Hz), 128.2 (d, $J_{F-C}$=3 Hz), 126.0 (d, J=3 Hz), 125.4 (d, $J_{F-C}$=3 Hz), 123.9 (dd, $J_{F-C}$=14, 3 Hz), 112.5 (d, $J_{F-C}$=5 Hz), 68.5 (CHMe$_2$), 61.5 (d, $J_{F-C}$=4 Hz, OMe), 21.56 (CHMe$_2$); $^{19}$F NMR (376 MHz, CDCl$_3$) δ −128.43 (dd, $J_{F-F}$=32.0, $J_{F-H}$=6.6 Hz), −142.27 (dd, dd, $J_{F-F}$=32.0, $J_{F-H}$=6.3 Hz). Anal. Calcd for C$_{16}$H$_{15}$ClF$_2$N$_2$O$_3$: C, 53.87; H, 4.24; N, 7.85. Found: C, 53.65; H, 4.28; N, 7.75.

Example 2c

Benzyl 4-amino-6-(4-chloro-2-fluoro-3-methoxyphenyl)-5-fluoropicolinate

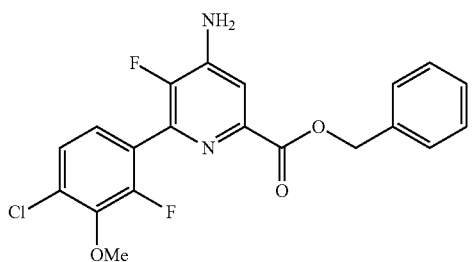

Benzyl 4,5-difluoro-6-(4-chloro-2-fluoro-3-methoxyphenyl)picolinate (4.99 g, 12.2 mmol) was slurried in DMSO (100 mL). Ammonia was bubbled through the solution for 30 min. After stirring overnight, the reaction mixture was poured into ice-water (500 mL). The product was extracted into EtOAc (3×150 mL). The combined organic extracts were washed with water (5×100 mL) and brine, dried (MgSO$_4$) and concentrated under reduced pressure to give a white solid (4.99 g, 101%); $^1$H NMR (400 MHz, CDCl$_3$) δ 7.52 (d, $J_{F-H}$=6.5 Hz, 1H, pyridine H3), 7.45-7.38 (m, 2H), 7.37-7.17 (m, 5H), 5.38 (s, 2H, CH$_2$Ph), 4.67 (br s, 2H, NH$_2$), 3.94 (d, $J_{F-H}$=1.1 Hz, 3H, OMe); $^{13}$C{$^1$H} NMR (101 MHz, CDCl$_3$) δ 164.4 (CO$_2$R), 153.9 (d, $J_{F-C}$=254 Hz), 147.6 (d, $J_{F-C}$=256 Hz), 144.4 (d, $J_{F-C}$=14 Hz), 144.0 (d, $J_{F-C}$=5 Hz), 142.2 (d, $J_{F-C}$=12 Hz), 140.4 (d, $J_{F-C}$=15 Hz), 135.6 (s), 129.5 (d, $J_{F-C}$=3 Hz), 128.5 (CH), 128.3 (CH), 128.3 (CH), 125.6 (d, $J_{F-C}$=3 Hz, CH), 125.2 (d, $J_{F-C}$=4 Hz, CH), 123.3 (dd, $J_{F-C}$=14, 4 Hz), 113.1 (d, $J_{F-C}$=4 Hz, C3), 67.3 (s, CH$_2$Ph), 61.5 (d, $J_{F-C}$=4 Hz, OMe); $^{19}$F{$^1$H} NMR (376 MHz, CDCl$_3$) δ −128.54 (dd, J=30.7, 5.2 Hz, F2'), −141.84 (dd, J=30.8, 6.5 Hz, F5). HRMS-ESI (m/z): [M]$^+$ calcd for C$_{20}$H$_{15}$ClF$_2$N$_2$O$_3$, 404.0739. found, 404.0757.

Example 2d

Benzyl 4-amino-6-(4-chloro-2-fluoro-3-methoxyphenyl)-5-fluoropicolinate

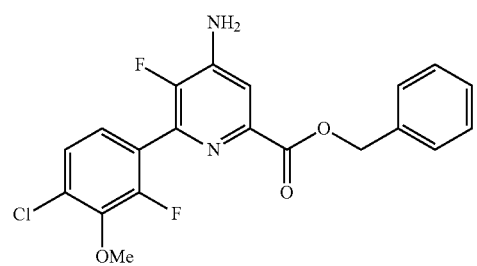 [SMILES: COc1c(Cl)ccc(-c2nc(C(=O)OCc3ccccc3)cc(N)c2F)c1F]

A solution of benzyl 4,5-difluoro-6-(4-chloro-2-fluoro-3-methoxyphenyl)picolinate (65.0 g, 0.16 mol, 87% purity) in DMSO (400 mL) was prepared in a 1 L 4-neck flask fitted with a mechanical stirrer, thermometer, ammonia input and gas outlet. Ammonia gas (8.1 g, 0.48 mol, 3 equiv) was added by bubbling through a Teflon tube below the surface of the DMSO solution for 20 min. During the ammonia addition, the reaction changed to a pink/light red color and the internal temperature rose to 30° C. After 5 h of stirring, additional ammonia gas (6.1 g, 0.36 mol, 2.25 equiv) was added over 20 min. After stiffing for an additional 2.5 h, HPLC analysis indicated complete consumption of starting material. Nitrogen was bubbled into the reaction mixture, and the reaction was allowed to stir overnight. The reaction mixture was filtered to remove salts formed during the reaction, and the solids were washed with DMSO (50 mL). To the DMSO solution was added water (225 mL) dropwise over 1 h. The resulting precipitate was filtered and then washed with DMSO/water (2:1, 2×40 mL) followed by water (2×50 mL). The solid was dried to give the title compound (55.35 g, 87%, 87% purity by HPLC (hexanophenone internal standard)).

Halogen Exchange

Example 3a

Propan-2-yl 4-amino-6-chloro-5-fluoropicolinate

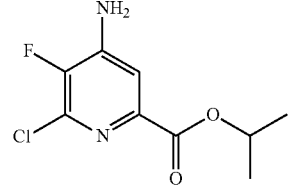

Propan-2-yl 4-amino-5,6-difluoropicolinate (4.25 g, 19.7 mmol) was dissolved in hydrochloric acid (HCl, 4 M in dioxane; 65 mL) in a 100 mL Hastalloy stiffed Parr reactor. The reactor was heated to 100° C. for 2 h. Upon standing at room temperature overnight, a yellow crystalline solid formed. This solid was not soluble in EtOAc, but did dissolve upon shaking with satd aq NaHCO₃ solution (500 mL) and EtOAc (300 mL). The aqueous layer was extracted with EtOAc (2×250 mL). The combined organic extracts were washed with water (5×50 mL) and then brine. The extracts were dried (MgSO₄) and concentrated under vacuum to provide an off-white solid. The crude product was purified by column chromatography (120 g silica column; 0-100% hexane-EtOAc gradient) to give a white solid (2.11 g, 46%): mp 190.7-192.4° C.; ¹H NMR (400 MHz, DMSO-d₆) δ 7.543 (d, $J_{F-H}$=5.7 Hz, 1H), 6.91 (br s, 2H, NH₂), 5.09 (septet, J=6 Hz, 1H, CHMe₂), 1.29 (d, J=6 Hz, 6H, CHMe₂); ¹³C{¹H} NMR (101 MHz, DMSO-d₆) δ 162.8 (CO₂R), 144.8 (d, $J_{F-C}$=12 Hz, C2/C4), 143.4 (d, $J_{F-C}$=254 Hz, C5), 142.7 (d, $J_{F-C}$=4.8 Hz, C2/C4), 136.5 (d, $J_{F-C}$=17 Hz, C6), 112.8 (d, $J_{F-C}$=5 Hz, C3), 68.9 (CHMe₂), 21.6 (Me); ¹⁹F NMR (376 MHz, DMSO-d₆) δ −141.0 (d, $J_{F-H}$=6 Hz). Anal. Calcd for C₉H₁₀ClFN₂O₂: C, 46.47; H, 4.33; N, 12.04. Found: C, 46.50; H, 4.33; N, 11.96.

Halogenation

Example 4a

Propan-2-yl 4-amino-3,6-dichloro-5-fluoropicolinate

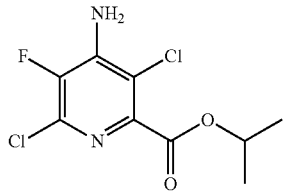 [SMILES: CC(C)OC(=O)c1nc(Cl)c(F)c(N)c1Cl]

Propan-2-yl 4-amino-6-chloro-5-fluoropicolinate (1.191 g, 5.12 mmol) was almost completely dissolved in CH₂Cl₂ (40 mL). Water (40 mL) was added. Chlorine was bubbled through the solution for 5 min. After 30 min, an aliquot of the reaction mixture was analyzed by GC, showing desired product and only 1.7% starting material. The aqueous layer was separated and extracted with CH₂Cl₂ (50 mL). The combined organic extracts were washed with satd aq NaHCO₃ solution and then brine. The extracts were dried (MgSO₄) and concentrated under reduced pressure to yield an orange oil. Flash chromatography (120 g silica column; 0-50% EtOAc-hexane gradient) afforded a bright yellow crystalline solid (394 mg, 28%): ¹H NMR (400 MHz, CDCl₃) δ 5.29 (septet, J=6.3 Hz, 1H, CHMe₂), 5.19 (br s, 2H, NH₂), 1.40 (d, J=6.3 Hz, 6H, CHMe₂); ¹³C{¹H} NMR (101 MHz, CDCl₃) δ 163.2 (CO₂R), 143.3 (d, $J_{F-C}$=5 Hz, C2), 142.8 (d, $J_{F-C}$=270 Hz, C5), 141.0 (d, $J_{F-C}$=26 Hz, C4), 135.3 (d, $J_{F-C}$=17 Hz, C6), 114.9 (s, C3), 70.6 (CHMe₂), 21.6 (s, Me); ¹⁹F NMR (376 MHz, CDCl₃) δ −136.5.

Example 4b

Propan-2-yl 4-amino-3,6-dichloro-5-fluoropicolinate

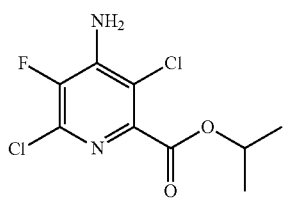 [SMILES: CC(C)OC(=O)c1nc(Cl)c(F)c(N)c1Cl]

Propan-2-yl 4-amino-6-chloro-5-fluoropicolinate (634 milligrams (mg), 2.73 mmol) was slurried in acetonitrile (11 mL). 1,3-Dichloro-5,5-dimethyl-hydantoin (303 mg, 1.54 mmol) was added as a solid, and the reaction mixture was stirred at reflux for 2.5 h. Additional 1,3-dichloro-5,5-dimethylhydantoin (50 mg, 0.25 mmol) was added, and the reaction mixture was stirred at reflux for an additional hour. Water (20 mL) was added. Acetonitrile was then removed by rotary evaporation to give an oily, yellow solid which was extracted with EtOAc (2×20 mL). The combined organic extracts were washed with 10% sodium bisulfite (NaHSO₃) solution, satd aq NaHCO₃ solution and brine, dried (MgSO₄) and concentrated under reduced pressure to provide a pale orange solid (671 mg, 92%): ¹H NMR (400 MHz, CDCl₃) δ 5.29 (septet, J=6.3 Hz, 1H, CHMe₂), 5.19 (br s, 2H, NH₂), 1.40 (d, J=6.3 Hz, 6H, CHMe₂); ¹⁹F NMR (376 MHz, CDCl₃) δ −136.5.

Example 4c

Methyl 4-amino-3-bromo-6-chloro-5-fluoropicolinate

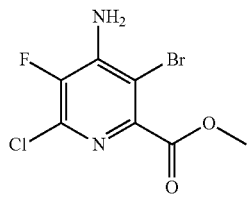

Methyl 4-amino-6-chloro-5-fluoropicolinate (1.0 g, 4.9 mmol) was combined with 1,3-dibromo-5,5-dimethylhydantoin (1.7 g, 5.9 mmol) in 1,2-dichloroethane (15 mL) and heated at reflux (83° C.) for 4 h. The cooled mixture was stirred with 10% NaHSO₃ solution and EtOAc (30 mL). The organic phase was separated, washed with water (2×20 mL), brine (10 mL), dried (Na₂SO₄) and concentrated. The residue was purified by silica gel chromatography (5-50% EtOAc-hexane) to give an orange solid (840 mg, 61%): mp 138-139° C.; EIMS m/z 282, 284; ¹H NMR (400 MHz, CDCl₃) δ 5.09 (s, 2H, NH₂), 3.97 (s, 3H, Me); ¹⁹F NMR (376 MHz, CDCl₃) δ −135.55 (s).

Example 4d

Methyl 4-amino-6-chloro-5-fluoro-3-iodopicolinate

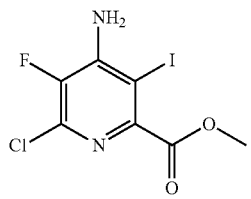

Methyl 4-amino-6-chloro-5-fluoropicolinate (2.2 g, 10.8 mmol) was dissolved in methyl alcohol (CH₃OH; 20 mL). The solution was treated with periodic acid (880 mg, 3.9 mmol) and iodine (2.2 g, 8.6 mmol) and then heated to reflux for 20 h. The mixture was cooled, and the volatiles were removed under vacuum. The residue was dissolved in EtOAc (50 mL) and then stirred with 10% NaHSO₃ solution (20 mL) for 10 min. The organic phase was separated and washed with brine (10 mL), dried (Na₂SO₄) and evaporated. The residue was purified by silica gel chromatography (5-50% EtOAc-hexane gradient) to give the title compound as a light orange solid (2.5 g, 70%): mp 149-151° C.; ESIMS m/z 330 ([M]$^+$); $^1$H NMR (400 MHz, CDCl$_3$) δ 5.17 (s, 2H, NH$_2$), 3.97 (s, 3H, OMe); $^{19}$F NMR (376 MHz, CDCl$_3$) δ −135.79 (s).

Example 4e

Propan-2-yl 4-amino-3-chloro-5-fluoro-6-(4-chloro-2-fluoro-3-methoxyphenyl)picolinate

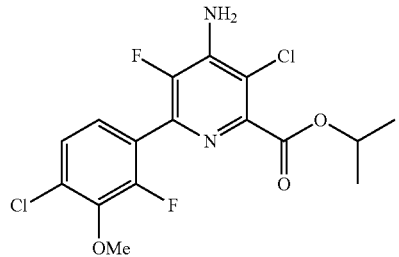 [SMILES: COc1c(Cl)ccc(-c2nc(C(=O)OC(C)C)c(Cl)c(N)c2F)c1F]

Propan-2-yl 4-amino-5-fluoro-6-(4-chloro-2-fluoro-3-methoxyphenyl)picolinate (3.065 g, 8.59 mmol) was dissolved in sulfuryl chloride (150 mL). The solution was stirred under nitrogen at room temperature for 8 h. During this time, a white precipitate formed. Hexane (100 mL) was added, and the mixture was stored overnight at −20° C. The product was filtered, washed with hexane and then slurried in EtOAc (100 mL). The organic suspension was neutralized with satd aq NaHCO$_3$ solution, which caused all solids to dissolve. The organic layer was separated and washed with 10% aq NaHSO$_3$ solution and brine, dried (MgSO$_4$), and concentrated under reduced pressure to give a white solid (1.962 g, 58%): mp 109-111° C.; $^1$H NMR (400 MHz, CDCl$_3$) δ 7.25 (m, 2H), 5.32 (septet, J=6.3 Hz, 1H, CHMe$_2$), 5.07 (br s, 2H), 3.97 (d, J$_{F-H}$=1.0 Hz, 3H, OMe), 1.40 (d, J=6.3 Hz, 6H, CHMe$_2$); $^{19}$F NMR (376 MHz, CDCl$_3$) δ −128.16 (dd, J$_{F-F}$=33.3 Hz, J$_{F-H}$=2.5 Hz, phenyl F), −138.35 (d, J$_{F-F}$=33.4 Hz, pyridine F5).

Example 4f

Benzyl 4-amino-3-chloro-6-(4-chloro-2-fluoro-3-methoxyphenyl)-5-fluoropicolinate

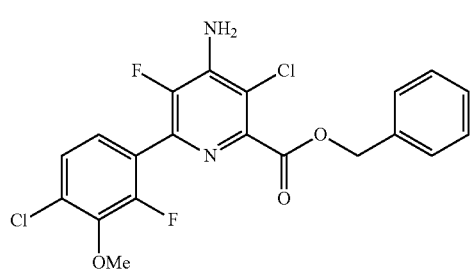 [SMILES: COc1c(Cl)ccc(-c2nc(C(=O)OCc3ccccc3)c(Cl)c(N)c2F)c1F]

Benzyl 4-amino-6-(4-chloro-2-fluoro-3-methoxyphenyl)-5-fluoropicolinate (2.07 g, 5.12 mmol) was slurried in acetonitrile (20 mL) in a scintillation vial. 1,3-Dichloro-5,5-dimethylhydantoin (554 mg, 2.181 mmol) was added as a solid, and the reaction mixture was stirred at reflux for 1 h. After cooling to room temperature, water (40 mL) was added to precipitate the product. The solid was collected on a Buchner funnel and washed with water. Drying under vacuum at 55° C. gave a white solid (2.187 g, 97%): $^1$H NMR (400 MHz, CDCl$_3$) δ 7.50-7.41 (m, 2H, aromatic), 7.41-7.20 (m, 5H, aromatic), 5.42 (s, 2H, CH$_2$Ph), 4.92 (br s, 2H, NH$_2$), 3.97 (d, J=1.2 Hz, 3H, OMe); $^{19}$F{$^1$H} NMR (CDCl$_3$) δ −128.19 (d, J=33.9 Hz, F2'), −137.79 (d, J=33.8 Hz, F5).

Example 4g

Benzyl 4-amino-3-chloro-6-(4-chloro-2-fluoro-3-methoxyphenyl)-5-fluoropicolinate

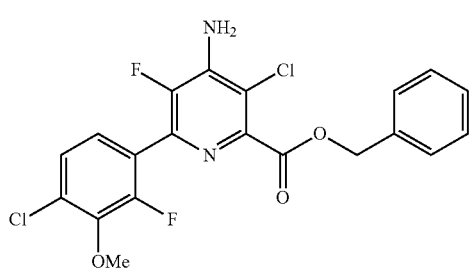 [SMILES: COc1c(Cl)ccc(-c2nc(C(=O)OCc3ccccc3)c(Cl)c(N)c2F)c1F]

A solution of benzyl 4-amino-6-(4-chloro-2-fluoro-3-methoxyphenyl)-5-fluoropicolinate (53.0 g, 0.131 mol, 95% purity) in acetonitrile (450 mL) was prepared in a 1 L 3-neck round bottom flask equipped with mechanical stirrer and thermometer. 1,3-Dichloro-5,5-dimethylhydantoin 14.2 g, 0.072 mol, 0.55 equiv) was added. The reaction mixture was heated at 80° C. for 3 h. The reaction mixture was allowed to cool to room temperature and was then added dropwise to a dilute sodium bisulfite (NaHSO$_3$) solution (990 mL, 7.5 g of NaHSO$_3$) over 1 h. The resulting precipitate was isolated by filtration, washed with acetonitrile-water (1:1 v/v, 2×50 mL) and then water (2×50 mL). The solid was dried to give a pale yellow powder (53.44 g, 94%, 96.1% HPLC purity (octanophenone internal standard)).

Example 4h

Propan-2-yl 4-amino-3-iodo-5-fluoro-6-(4-chloro-2-fluoro-3-methoxyphenyl)picolinate

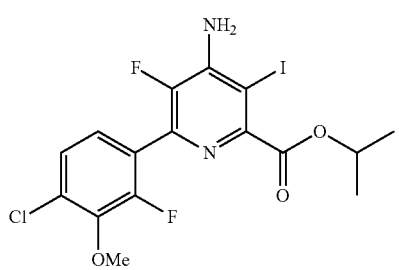 [SMILES: COc1c(Cl)ccc(-c2nc(C(=O)OC(C)C)c(I)c(N)c2F)c1F]

Propan-2-yl 4-amino-5-fluoro-6-(4-chloro-2-fluoro-3-methoxyphenyl)picolinate (600 mg, 1.682 mmol) was dissolved in acetic acid (5.6 mL). Sodium acetate (1.5 g, 18.50 mmol) was added followed by iodine monochloride (2.2 g, 13.45 mmol). An exotherm of approximately 10° C. was observed during the addition. The reaction mixture was heated at 80° C. for 20 h. The reaction mixture was then diluted with water and extracted with EtOAc. The organic layer was washed with water, satd aq NaHCO₃ solution, dried (MgSO₄) and then concentrated to dryness. The residue was applied to a silica gel column (80 g) then eluted (0-70% acetone-hexanes gradient) to give an orange solid (343 mg, 42%): mp 134-135° C.; $^1$H NMR (400 MHz, acetone-d₆) δ 7.41 (dd, J=8.5, 1.6 Hz, 1H), 7.33 (dd, J=8.5, 6.8 Hz, 1H), 6.29 (s, 2H), 5.29-5.14 (septet, 1H), 3.98 (d, J=1.1 Hz, 3H), 1.37 (d, J=6.3 Hz, 6H); EIMS m/z 396.

Example 4i

Propan-2-yl 4-amino-3-bromo-5-fluoro-6-(4-chloro-2-fluoro-3-methoxyphenyl)picolinate

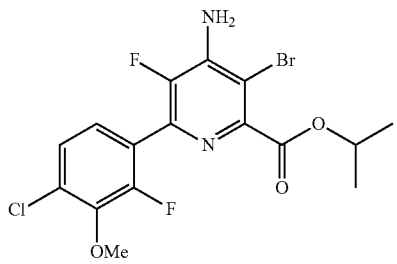

Propan-2-yl 4-amino-5-fluoro-6-(4-chloro-2-fluoro-3-methoxyphenyl)picolinate (500 mg, 1.402 mmol) was dissolved in dichloromethane (3.2 mL). N-Bromo-succinimide (299 mg, 1.682 mmol) was added, and the solution was stirred at ambient temperature for 20 h. The reaction mixture was then concentrated to dryness. The residue was purified by chromatography (40 g silica gel column; 0-70% EtOAc-hexanes) to give a tan solid (504 mg, 83%): $^1$H NMR (400 MHz, DMSO-d₆) δ 7.47 (dd, J=8.5, 1.6 Hz, 1H), 7.29 (dd, J=8.5, 7.1 Hz, 1H), 7.01 (s, 2H), 5.22-5.10 (m, 1H), 3.93 (d, J=0.9 Hz, 3H), 1.32 (d, J=6.3 Hz, 6H); EIMS m/z 350.

Coupling

Example 5a

Propan-2-yl 4-amino-3-chloro-5-fluoro-6-(4-chloro-2-fluoro-3-methoxyphenyl)picolinate

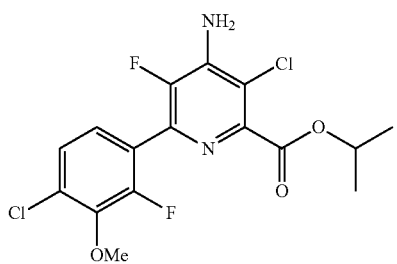

A 50 mL Schlenk flask was charged with propan-2-yl 4-amino-3,6-dichloro-5-fluoropicolinate (2.162 g, 8.09 mmol), 2-(4-chloro-2-fluoro-3-methoxyphenyl)-1,3,2-dioxaborinane (2.775 g, 11.35 mmol) and CsF (2.601 g, 17.12 mmol). Acetonitrile (20 mL) and water (7 mL) were added. The solution was evacuated/backfilled with nitrogen (5×). Solid bis(triphenylphosphine)palladium(II) dichloride (Pd(PPh₃)₂Cl₂; 281 mg, 4.9 mol %) was added. The solution was evacuated/backfilled with nitrogen (5×) and then heated at 70° C. under nitrogen for 3 h. After 3 h, the reaction mixture was allowed to cool to room temperature. The aqueous layer was separated. Water (20 mL) was added to the organic layer. The resulting dark brown precipitate was filtered and washed with water. The solid was dissolved in EtOAc (60 mL) and filtered to remove a small amount of black solid. The EtOAc solution was treated with activated carbon (175 mg) and filtered to give a wine-colored solution. Evaporation under reduced pressure gave a dark red solid. Purification (120 g silica column; 0-50% EtOAc-hexane gradient) gave a white solid (2.59 g, 82%): mp 110.6-112.1° C.; $^1$H NMR (400 MHz, CDCl₃) δ 7.25 (m, 2H), 5.32 (septet, J=6.3 Hz, 1H, CHMe₂), 5.07 (br s, 2H), 3.97 (d, $J_{F-H}$=1.0 Hz, 3H, OMe), 1.40 (d, J=6.3 Hz, 6H, CHMe₂); $^{13}$C{$^1$H} NMR (101 MHz, CDCl₃) δ 164.2 (CO₂R), 153.8 (d, $J_{F-C}$=254 Hz, C5/C2'), 145.5 (d, $J_{F-C}$=258 Hz, C5/C2'), 145.0 (d, $J_{F-C}$=5 Hz), 144.4 (d, $J_{F-C}$=14 Hz), 140.0 (d, $J_{F-C}$=13 Hz), 137.5 (d, $J_{F-C}$=14 Hz), 129.7 (d, $J_{F-C}$=3 Hz), 125.4 (d, $J_{F-C}$=2 Hz, C5'/C6'), 125.2 (d, $J_{F-C}$=3 Hz, C5'C6'), 122.7 (dd, $J_{F-C}$=14, 4 Hz, C1'), 114.6 (C3), 70.2 (CHMe₂), 61.5 (d, $J_{F-C}$=4 Hz, OMe), 21.6 (CHMe₂); $^{19}$F NMR (376 MHz, CDCl₃) δ −128.16 (dd, $J_{F-F}$=33.3 Hz, $J_{F-H}$=2.5 Hz, phenyl F), −138.35 (d, $J_{F-F}$=33.4 Hz, pyridine F5). Anal. Calcd for C₁₆H₁₄Cl₂F₂N₂O₃: C, 49.12; H, 3.61; N, 7.16. Found: C, 49.30; H, 3.69; N, 7.08. The product was found to be 97.5% pure by HPLC.

Example 5b

Propan-2-yl 4,5-dichloro-6-(4-chloro-2-fluoro-3-methoxyphenyl)-picolinate

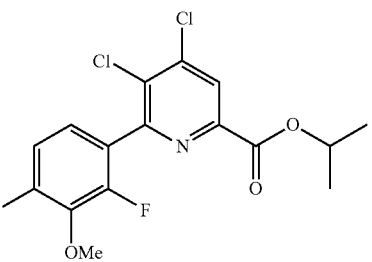

A 100 mL Schlenk flask was charged with propan-2-yl 4,5,6-trichloropicolinate (10.46 g, 39.0 mmol), 2-(4-chloro-2-fluoro-3-methoxyphenyl)-1,3,2-dioxaborinane (13.27 g, 54.3 mmol) and CsF (11.76 g, 77.0 mmol). Acetonitrile (75 mL) and water (25 mL) were added. The reaction mixture was evacuated/backfilled with N₂ (5×). Solid Pd(PPh₃)₂Cl₂ (1.331 g, 1.896 mmol) was added. The solution was evacuated/backfilled with N₂ (5×) and then stirred at reflux for 2 h. A white solid precipitated upon cooling to room temperature. The solid was filtered, washed with water and dried in air (10.56 g, 69%): mp 123.8-127.7° C.; $^1$H NMR (400 MHz, CDCl₃) δ 8.20 (s, 1H, pyridine), 7.28 (dd, $J_{H-H}$=8.5 Hz, $J_{F-H}$=1.6 Hz, 1H), 7.13 (dd, $J_{H-H}$=8.5 Hz, $J_{F-H}$=6.8 Hz, 1H), 5.32 (septet, J=6.3 Hz, 1H, CHMe₂), 3.99 (d, J=1.2 Hz, 3H, OMe), 1.41 (d, J=6.3 Hz, 6H, CHMe₂); $^{13}$C{$^1$H} NMR (101 MHz, CDCl₃) δ 162.7 (CO₂R), 153.8, 153.6 (d, $J_{F-C}$=253 Hz, C2'), 146.7, 144.5 (d, $J_{F-C}$=13 Hz), 144.0, 134.0, 130.0 (d, $J_{F-C}$=3.4 Hz), 125.9, 125.3 (d, $J_{F-C}$=3 Hz), 125.1 (d, $J_{F-C}$=3 Hz), 70.4

(CHMe$_2$), 61.6 (d, J$_{F-C}$=4 Hz, OMe), 21.7 (CHMe$_2$). Anal. Calcd for C$_{16}$H$_{13}$Cl$_3$NO$_3$: C, 48.94; H, 3.34; N, 3.57. Found: C, 48.91; H, 3.50; N, 3.51.

Example 5c

Methyl 4,5-dichloro-6-ethylpicolinate

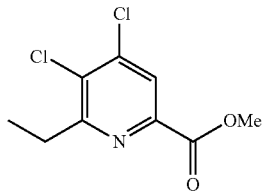

A 100 mL three-neck flask equipped with a reflux condenser and nitrogen inlet was charged with methyl 4,5,6-trichloropicolinate (2.40 g, 9.98 mmol). Anhydrous THF (50 mL) was added followed by N,N-dimethylethanolamine (0.20 g). The reaction mixture was sparged with nitrogen for 15 min. Solid Pd(PPh$_3$)$_2$Cl$_2$ (140 mg, 0.2 mmol) was added. The reaction mixture was stirred under nitrogen for 20 min. Diethylzinc (1 M solution in hexanes; 10 mL, 10 mmol) was added in 2 mL portions. When starting material was no longer observed through analysis by GC, the reaction mixture was quenched with water and extracted into EtOAc. The combined organic extracts were washed with brine, dried (MgSO$_4$) and concentrated under reduced pressure to a white solid (2.34 g). Analysis by GC-MS showed the solid contained 11% starting methyl 4,5,6-trichloropicolinate. $^1$H NMR (400 MHz, CDCl$_3$) δ 8.06 (s, 1H, pyridine H), 4.01 (s, 3H, CO$_2$Me), 3.10 (q, J=8 Hz, 2H, CH$_2$), 1.33 (t, J=8 Hz, 3H, CH$_2$CH$_3$); $^{13}$C{$^1$H} NMR (101 MHz, CDCl$_3$) δ 164.4, 162.8, 145.4, 143.3, 132.9, 124.5 (C3), 53.1 (CO$_2$Me), 30.0 (CH$_2$), 12.3 (CH$_2$CH$_3$).

Example 5d

Benzyl 4,5-dichloro-6-(4-chloro-2-fluoro-3-methoxyphenyl)picolinate

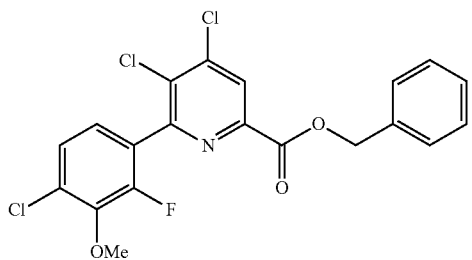 [SMILES: COc1c(Cl)ccc(-c2nc(C(=O)OCc3ccccc3)cc(Cl)c2Cl)c1F]

A 250 mL three-neck flask equipped with a reflux condenser and nitrogen inlet was charged with benzyl 4,5,6-trichloropicolinate (17.77 g, 56.10 mmol), 2-(4-chloro-2-fluoro-3-methoxyphenyl)-1,3,2-dioxaborinane (19.20 g, 79.0 mmol) and CsF (17.04 g, 112.0 mmol). Acetonitrile (100 mL) and water (30 mL) were added. The reaction mixture was evacuated/backfilled with nitrogen (5x). Solid Pd(PPh$_3$)$_2$Cl$_2$ (1.724 g, 2.456 mmol) was added. The solution was evacuated/backfilled with nitrogen (5x) and then stirred at reflux for 90 min. A white solid precipitated upon cooling to room temperature. The solid was filtered, washed with water and dried in air (18.66 g, 75%): $^1$H NMR (400 MHz, CDCl$_3$) δ 8.23 (s, 1H, pyridine H), 7.52-7.32 (m, 5H, phenyl), 7.27 (dd, J$_{H-H}$=8.4 Hz, J$_{F-H}$=1.7 Hz, 1H, aromatic), 7.10 (dd, J$_{H-H}$=8.4 Hz, J$_{F-H}$=6.8 Hz, 1H, aromatic), 5.44 (s, 2H, CH$_2$Ph), 3.98 (d, JJ$_{F-H}$=1.3 Hz, 3H, OMe); $^{13}$C{$^1$H} NMR (101 MHz, CDCl$_3$) δ 163.0, 153.7, 153.5 (d, J$_{F-C}$=253 Hz, C2'), 146.0, 144.5 (d, J$_{F-C}$=13 Hz), 144.1, 135.0, 134.2, 129.9 (d, J$_{F-C}$=3 Hz), 128.5, 126.1, 125.8 (d, J$_{F-C}$=14 Hz), 125.3 (d, J$_{F-C}$=3 Hz), 124.9 (d, J$_{F-C}$=2 Hz), 67.9 (CH$_2$), 61.5 (d, J$_{F-C}$=4 Hz, OMe). Anal. Calcd for C$_{20}$H$_{13}$Cl$_3$FNO$_3$: C, 54.51; H, 2.97; N, 3.18. Found: C, 54.60; H, 3.08; N, 3.16.

Example 5e

Benzyl 4,5-dichloro-6-(4-chloro-2-fluoro-3-methoxyphenyl)picolinate

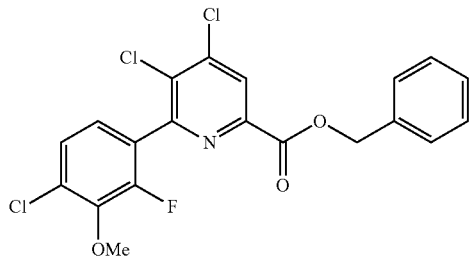

A 22-L straight wall reactor equipped with a mechanical stirrer was charged with tap water (3403 g). Dipotassium phosphate (K$_2$HPO$_4$; 2596 g, 14.9 mol) was then added, and the mixture was stirred until all solids dissolved while being purged with a nitrogen stream. After all the solids had dissolved, acetonitrile (8173 g) was loaded into the reactor. To a separate 30-L straight-wall jacketed reactor equipped with a bottom drain and a mechanical overhead stirrer was loaded 2-(4-chloro-2-fluoro-3-methoxyphenyl)-1,3,2-dioxaborinane (1724 g, 7.01 mol) and benzyl 4,5,6-trichloropicolinate (1630 g, 4.97 mol). The reactor was evacuated and filled with nitrogen (3x). The acetonitrile/H$_2$O mixture containing K$_2$HPO$_4$ was then transferred into the 30-L reactor, and the lines were rinsed with acetonitrile (1434 g). The slurry was sparged with nitrogen for 30 min, and then triphenylphosphine (114.8 g, 0.44 mol) was added. The slurry was then sparged with nitrogen for 15 min followed by addition of bis(benzonitrile)palladium(II) chloride (83.8 g, 0.22 mol). The bright yellow slurry was sparged with nitrogen for 15 min, and then the mixture was heated to 74-75° C. After stirring at 74° C. for 3.3 h the reaction was deemed complete by HPLC analysis. At this stage the reactor cool-down temperature was set to 5° C. and immediately, cold water (4448 g, approximately 3° C.) was added to the reactor. The resulting precipitate was filtered to give a cream-white colored cake. The filter cake was washed with cold acetonitrile/H$_2$O (3345 g, 1.4:1, 8-10° C.) to afford an off-white wet cake. The cake was dried under a stream of nitrogen to a constant weight of 2044 g. HPLC analysis using an internal standard (tetraphenylethylene) showed the product was 90.0% pure and contained 1840 g (84.0%) of the product.

Purification of Ammonium Salts

Example 6a

Propan-2-yl 4-amino-6-(4-chloro-2-fluoro-3-methoxyphenyl)-5-fluoropicolinate

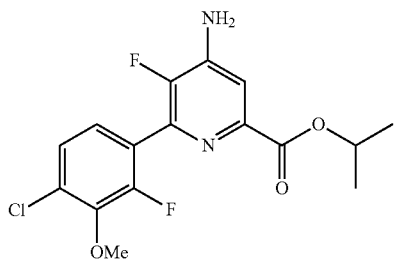

Propan-2-yl 4-amino-5-fluoro-6-(4-chloro-2-fluoro-3-methoxyphenyl)picolinate (1.50 g, 71% purity by LC area) was added to tetrahydrofuran (THF; 10 mL) and heated to 40° C. to provide a clear yellow solution. The solution was allowed to cool to room temperature and HCl (4 M in dioxane; 1.3 mL, 5.2 mmol) was added. After addition of HCl, solids precipitated from the solution and the reaction mixture was cooled to 0° C. The solids were isolated by vacuum filtration and washed with cold THF (5 mL). The salt wet cake was added to THF (10 mL) and water (5 mL). Triethylamine (Et$_3$N, 0.8 mL, 5.7 mmol) was added to the mixture and the reaction mixture formed a clear biphasic solution. The reaction mixture was transferred to a separatory funnel, and the organic layer was separated. Hexanes (20 mL) was added to the organic layer and solids precipitated from solution. The reaction mixture was cooled to 0° C. and allowed to stir for 30 min. The solids were isolated by vacuum filtration, washed with hexanes (10 mL), and dried in a vacuum oven at 40° C. to provide propan-2-yl 4-amino-6-(4-chloro-2-fluoro-3-methoxyphenyl)-5-fluoropicolinate as a white solid (0.90 g, 89% purity by LC area): mp 174-176° C.; $^1$H NMR (400 MHz, CDCl$_3$) δ 7.54 (d, J=6.4 Hz, 1H), 7.34-7.22 (m, 2H), 5.27 (septet, J=6.3 Hz, 1H), 4.56 (br s, 2H), 3.97 (d, J=1.0 Hz, 3H), 1.39 (d, J=6.3 Hz, 6H); $^{13}$C NMR (101 MHz, CDCl$_3$) δ 164.03, 154.07 (d, J=253.7 Hz), 147.70 (d, J=256.1 Hz), 144.92 (d, J=5.0 Hz), 144.48 (d, J=13.9 Hz), 142.01 (d, J=12.2 Hz), 140.58 (d, J=14.4 Hz), 129.59 (d, J=3.4 Hz), 125.85 (d, J=3.7 Hz), 125.29 (d, J=3.8 Hz), 123.57 (dd, J=14.1, 3.7 Hz), 112.85 (d, J=3.7 Hz), 69.58 (s), 61.63 (d, J=4.5 Hz), 21.86 (s); $^{19}$F NMR (376 MHz, CDCl$_3$) δ −128.44 (d, J=32.7 Hz), −142.30 (d, J=31.3 Hz).

Example 6b

Propan-2-yl 4-amino-3-chloro-6-(4-chloro-2-fluoro-3-methoxyphenyl)5-fluoropicolinate

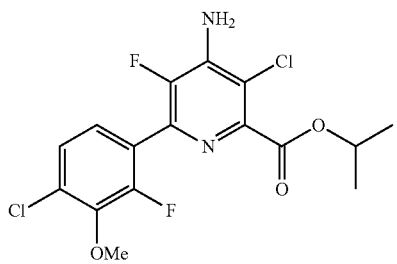 [SMILES: COc1c(Cl)ccc(-c2nc(C(=O)OC(C)C)c(Cl)c(N)c2F)c1F]

Propan-2-yl 4-amino-3-chloro-5-fluoro-6-(4-chloro-2-fluoro-3-methoxyphenyl)picolinate (1.75 g, 95% purity by LC area) was added to dichloromethane (15 mL), and the mixture was heated to 40° C. to provide a clear yellow solution. The solution was allowed to cool to room temperature and HCl (4 M in dioxane; 1.25 mL, 5 mmol) was added. After addition of HCl, solids precipitated from the solution, and the reaction mixture was cooled to 0° C. The solid was isolated by vacuum filtration and washed with cold dichloromethane (5 mL). The salt wet cake was added to dichloromethane (10 mL) and water (5 mL). Et$_3$N (0.6 mL, 4.3 mmol) was added to the mixture, and the reaction mixture formed a clear biphasic solution. The reaction mixture was transferred to a separatory funnel, and the organic layer was separated. Hexanes (20 mL) was added to the organic layer and solids precipitated from solution. The reaction mixture was cooled to 0° C., and the solids were isolated by vacuum filtration and washed with hexanes (10 mL). The solid was dried in a vacuum oven at 40° C. to provide propan-2-yl 4-amino-3-chloro-6-(4-chloro-2-fluoro-3-methoxyphenyl)-5-fluoropicolinate as a white solid. (1.02 g, 99% purity by LC area): mp 115-117° C.; $^1$H NMR (400 MHz, CDCl$_3$) δ 7.31-7.22 (m, 2H), 5.32 (septet, J=6.3 Hz, 1H), 4.93 (br s, 2H), 3.98 (d, J=1.1 Hz, 3H), 1.41 (d, J=6.3 Hz, 6H); $^{13}$C NMR (101 MHz, CDCl$_3$) δ 164.28, 153.93 (d, J=254.4 Hz), 145.79 (d, J=230.6 Hz), 145.23 (d, J=4.9 Hz), 144.44 (d, J=13.8 Hz), 139.97 (d, J=13.5 Hz), 137.72 (d, J=13.8 Hz), 129.90 (d, J=3.4 Hz), 125.59 (d, J=3.2 Hz), 125.41 (d, J=3.7 Hz), 122.82 (dd, J=14.0, 4.4 Hz), 114.82, 70.36, 61.66 (d, J=4.7 Hz), 21.76; $^{19}$F NMR (376 MHz, CDCl$_3$) δ −128.15 (d, J=34.1 Hz), −138.44 (d, J=34.1 Hz).

Example 6c

Methyl 4-amino-6-(4-chloro-2-fluoro-3-methoxyphenyl)-5-fluoropicolinate

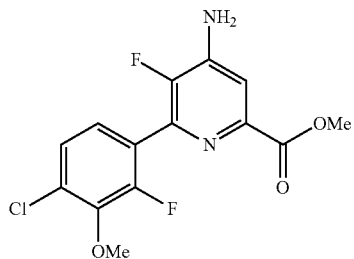 [SMILES: COC(=O)c1cc(N)c(F)c(-c2ccc(Cl)c(OC)c2F)n1]

Benzyl 4-amino-5-fluoro-6-(4-chloro-2-fluoro-3-methoxyphenyl)picolinate (3.00 g, 7.41 mmol) was added to CH$_3$OH (35 mL). Sodium methoxide (25 wt % in CH$_3$OH; 2.0 mL, 8.9 mmol) was added to the reaction mixture and allowed to stir for 24 h. Water (50 mL) was added to the reaction mixture and the mixture was concentrated under reduced pressure to remove most of the CH$_3$OH. The mixture was extracted with EtOAc (2×40 mL), and the combined organic layers were washed with water (40 mL) and satd sodium chloride (40 mL) and concentrated under reduced pressure to provide methyl 4-amino-6-(4-chloro-2-fluoro-3-methoxyphenyl)-5-fluoropicolinate as a pale yellow solid (1.86 g; 67% purity by LC area).

Methyl 4-amino-5-fluoro-6-(4-chloro-2-fluoro-3-methoxyphenyl)picolinate (1.50 g, 67% purity by LC area) was added to THF (10 mL) and dichloromethane (5 mL), and the mixture was heated to 40° C. to provide a clear yellow solution. The solution was allowed to cool to room temperature and HCl (4 M in dioxane; 1.4 mL, 5.6 mmol) was added. After addition of HCl, solids precipitated from the solution, and the reaction mixture was cooled to 0° C. The solid was isolated by vacuum filtration and washed with cold THF (5 mL). The salt wet cake was added to THF (25 mL) and water (10 mL). Et₃N (0.8 mL, 5.7 mmol) was added to the mixture, and the reaction mixture formed a clear biphasic solution. The reaction mixture was transferred to a separatory funnel, and the organic layer was separated and concentrated to a solution of ~10 mL. Hexanes (20 mL) was added to the organic layer, and solids precipitated from solution. The reaction mixture was cooled to 0° C., and the solids were isolated by vacuum filtration and washed with hexanes (10 mL). The solid was dried in a vacuum oven at 40° C. to provide methyl 4-amino-6-(4-chloro-2-fluoro-3-methoxyphenyl)-5-fluoropicolinate as a white solid (0.53 g, 89% purity by LC area): mp 203-204° C.; ¹H NMR (400 MHz, CDCl₃) δ 7.60 (d, J=6.4 Hz, 1H), 7.28-7.25 (m, 2H), 4.58 (br s, 2H), 3.97 (d, J=1.1 Hz, 3H), 3.96 (s, 3H); ¹³C NMR (101 MHz, CDCl₃) δ 165.27, 154.05 (d, J=254.1 Hz), 147.83 (d, J=256.3 Hz), 144.56 (d, J=13.7 Hz), 144.31 (d, J=5.1 Hz), 142.16 (d, J=12.4 Hz), 140.63 (d, J=14.5 Hz), 129.69 (d, J=3.5 Hz), 125.63 (d, J=3.1 Hz), 125.41 (d, J=3.7 Hz), 123.43 (dd, J=14.1, 3.6 Hz), 113.05 (d, J=3.7 Hz), 61.64 (d, J=4.5 Hz), 52.98; ¹⁹F NMR (376 MHz, CDCl₃) δ −128.71 (d, J=28.6 Hz), −141.94 (d, J=28.6 Hz).

Example 6d

Methyl 4-amino-3-chloro-6-(4-chloro-2-fluoro-3-methoxyphenyl) 5-fluoropicolinate

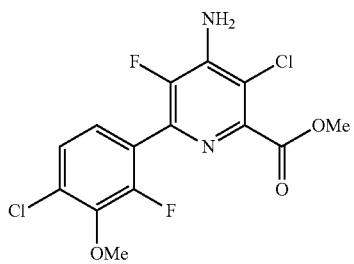 [SMILES: COC(=O)c1nc(-c2ccc(Cl)c(OC)c2F)c(F)c(N)c1Cl]

Benzyl 4-amino-3-chloro-6-(4-chloro-2-fluoro-3-methoxyphenyl)-5-fluoropicolinate (3.00 g, 6.83 mmol) was added to CH₃OH (35 mL). Sodium methoxide (25 wt % in CH₃OH; 1.9 mL, 8.2 mmol) was added to the reaction mixture, and the reaction mixture was allowed to stir for 24 h. Water (50 mL) was added to the reaction mixture, and the mixture was concentrated under reduced pressure to remove most of the CH₃OH. The mixture was extracted with EtOAc (2×40 mL), and the combined organic layers were washed with water (40 mL) and satd sodium chloride (40 mL). Concentration of the volatiles under reduced pressure provided methyl 4-amino-3-chloro-6-(4-chloro-2-fluoro-3-methoxyphenyl)-5-fluoropicolinate as a pale yellow solid (2.04 g, 88% purity by LC area).

Methyl 4-amino-3-chloro-6-(4-chloro-2-fluoro-3-methoxyphenyl)-5-fluoropicolinate (1.25 g, 88% purity by LC area) was added to dichloromethane (15 mL) and THF (3 mL), and the mixture was heated to 40° C. to provide a clear yellow solution. The solution was allowed to cool to room temperature, and HCl (4 M in dioxane; 0.95 mL, 3.8 mmol) was added. After addition of HCl, solids precipitated from the solution, and the reaction mixture was cooled to 0° C. The solid was isolated by vacuum filtration and washed with cold dichloromethane (5 mL). The salt wet cake was added to dichloromethane (20 mL) and water (10 mL). Et₃N (0.6 mL, 4.3 mmol) was added to the mixture, and the reaction mixture formed a clear biphasic solution. The reaction mixture was transferred to a separatory funnel, and the organic layer was separated and concentrated under reduced pressure to a solution of ~10 mL. Hexanes (20 mL) was added to the organic layer and solids precipitated from solution. The reaction mixture was cooled to 0° C., and the solids were isolated by vacuum filtration and washed with hexanes (10 mL). The solid was dried in a vacuum oven at 40° C. to provide methyl 4-amino-3-chloro-6-(4-chloro-2-fluoro-3-methoxyphenyl)-5-fluoropicolinate as a white solid (0.51 g, 96% purity by LC area): mp 170-171° C.; ¹H NMR (400 MHz, CDCl₃) δ 7.30-7.20 (m, 2H), 4.98 (br s, 2H), 3.98 (m, 6H); ¹³C NMR (101 MHz, CDCl₃) δ 164.67, 153.95 (d, J=254.7 Hz), 145.93 (d, J=245.8 Hz), 144.57 (s), 143.65 (d, J=4.6 Hz), 140.21 (d, J=13.3 Hz), 137.71 (d, J=13.9 Hz), 130.02 (d, J=3.5 Hz), 125.49 (d, J=7.1 Hz), 125.49, 122.70 (dd, J=14.1, 4.3 Hz), 115.89 (d, J=1.5 Hz), 61.67 (d, J=4.5 Hz), 53.06; ¹⁹F NMR (376 MHz, CDCl₃) δ −128.34 (d, J=31.3 Hz), −137.60 (d, J=32.7 Hz).

Example 6e

Benzyl 4-amino-6-(4-chloro-2-fluoro-3-methoxyphenyl)-5-fluoropicolinate

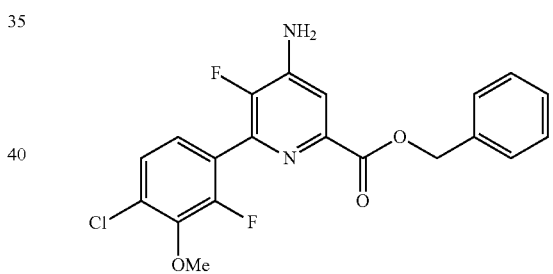

A slurry of benzyl 4-amino-5-fluoro-6-(4-chloro-2-fluoro-3-methoxyphenyl)-2-pyridinecarboxylate (98 g, 0.209 mol, 86.5% purity) and THF (300 mL) was gently heated to 28° C. to give a clear amber solution. The solution was allowed to cool to 20° C., and HCl (4 M in 1,4-dioxane; 55 mL, 0.219 mol, 1.05 equiv) was added via syringe over 1 min. The solution rapidly became cloudy with solid formation, and the temperature of the mixture reached 28° C. The mixture was cooled to below 10° C. The precipitate was filtered and rinsed with cold THF (2×40 mL) to give a white solid (120.4 g). This solid was stirred with THF (300 mL) and water (100 mL). To this slurry was added Et₃N (30.5 mL, 0.219 mol) via syringe over 1 min, and the solids dissolved to give a cloudy mixture. The organic layer was separated. Hexanes (450 mL) was added with stirring, and the solution was cooled to below 10° C. The resulting precipitate was filtered and rinsed with hexanes (2×40 mL) to give a white solid (76.1 g, 95.1 wt % HPLC purity (hexanophenone internal standard)). An additional 7.56 g of 93.9% pure product was obtained from concentration of the filtrate. The ¹H and ¹⁹F NMR spectra of the isolated product were identical to that observed in example 2c.

Example 6f

Benzyl 4-amino-3-chloro-6-(4-chloro-2-fluoro-3-methoxyphenyl)-5-fluoropicolinate

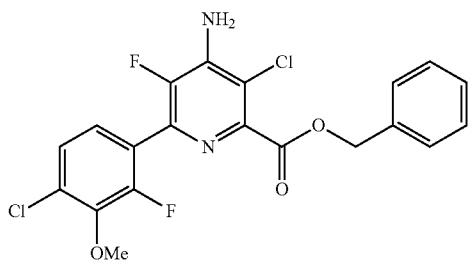 [SMILES: COc1c(Cl)ccc(-c2nc(C(=O)OCc3ccccc3)c(Cl)c(N)c2F)c1F]

To a solution of benzyl 4-amino-3-chloro-6-(4-chloro-2-fluoro-3-methoxyphenyl)-5-fluoropicolinate (5.00 g, 87% purity by LC area, 88 wt % by LC assay) in dichloromethane (25 mL) was added HCl (4 M in 1,4-dioxane; 3.1 mL, 12.4 mmol) via syringe. The solution became cloudy with solids formation after 1 min of stirring. The mixture was cooled in an ice bath to below 10° C., filtered and rinsed with cold dichloromethane (5 mL) to give a white solid. This solid was slurried with dichloromethane (30 mL) and water (15 mL), and $Et_3N$ (1.98 mL, 14.2 mmol) was added. The solids dissolved to give a two phase mixture. After stirring for 15 min, the mixture was transferred to a separatory funnel and the phases were allowed to separate over 15 min. The organic layer was separated, hexanes (60 mL) was added, and the mixture was cooled to below 10° C. The solution quickly became cloudy and solids precipitated from the mixture. Vacuum filtration of the mixture provided a white solid, which was dried in a vacuum oven at 40° C. to afford benzyl 4-amino-3-chloro-6-(4-chloro-2-fluoro-3-methoxyphenyl)-5-fluoro-2-pyridinecarboxylate as a white solid. (3.11 g, 70%, 97% purity by LC area, 97 wt % by LC assay). The $^1H$ and $^{19}F$ NMR spectra of the isolated product were identical to that observed in example 4f.

What is claimed is:

1. A compound of the formula

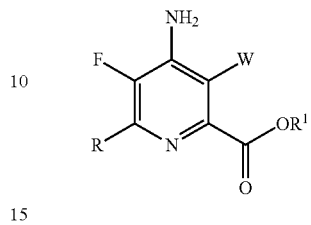

wherein $Y^2$ represents H, Br or I, and R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy and $R^1$ represents $C_1$-$C_{12}$ alkyl or an unsubstituted or substituted $C_7$-$C_{11}$ arylalkyl.

2. The compound of claim 1 wherein R is 4-chloro-2-fluoro-3-methoxyphenyl.

3. The compound of claim 1 wherein $R^1$ is methyl, isopropyl, or benzyl.

4. The compound of claim 1 selected from the group consisting of:
propan-2-yl 4-amino-5-fluoro-6-(4-chloro-2-fluoro-3-methoxyphenyl)-picolinate,
benzyl 4-amino-6-(4-chloro-2-fluoro-3-methoxyphenyl)-5-fluoro-picolinate,
propan-2-yl 4-amino-3-iodo-5-fluoro-6-(4-chloro-2-fluoro-3-methoxyphenyl)picolinate,
propan-2-yl 4-amino-3-bromo-5-fluoro-6-(4-chloro-2-fluoro-3-methoxyphenyl)picolinate, and
methyl 4-amino-6-(4-chloro-2-fluoro-3-methoxyphenyl)-5-fluoropicolinate.

\* \* \* \* \*